US011649217B2

(12) United States Patent
Chen et al.

(10) Patent No.: US 11,649,217 B2
(45) Date of Patent: *May 16, 2023

(54) CRYSTALLINE FORMS OF GSK1278863, PREPARATION METHOD AND PHARMACEUTICAL USE THEREOF

(71) Applicant: GLAXOSMITHKLINE INTELLECTUAL PROPERTY (NO.2) LIMITED, Brentford (GB)

(72) Inventors: Minhua Chen, Suzhou (CN); Yanfeng Zhang, Suzhou (CN); Jinqiu Wang, Suzhou (CN); Xiaoyu Zhang, Suzhou (CN)

(73) Assignee: GlaxoSmithKline Intellectual Property (NO.2) Limited, Brentford (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/174,006

(22) Filed: Feb. 11, 2021

(65) Prior Publication Data

US 2021/0230124 A1 Jul. 29, 2021

Related U.S. Application Data

(63) Continuation of application No. 16/818,368, filed on Mar. 13, 2020, now Pat. No. 11,117,871, which is a continuation of application No. PCT/CN2018/078766, filed on Mar. 13, 2018.

(30) Foreign Application Priority Data

Sep. 15, 2017 (CN) .......................... 201710835313.2

(51) Int. Cl.
C07D 239/62 (2006.01)

(52) U.S. Cl.
CPC ........ C07D 239/62 (2013.01); C07B 2200/13 (2013.01)

(58) Field of Classification Search
CPC .................................................. C07D 239/62
See application file for complete search history.

(56) References Cited

U.S. PATENT DOCUMENTS 11,117,871 B2 * 9/2021 Chen .................... A61K 31/515

FOREIGN PATENT DOCUMENTS

| CN | 101505752 A | 8/2009 |
| JP | 2003-519698 | 6/2003 |
| JP | 2009-541351 | 11/2009 |
| WO | WO 01051919 | 7/2001 |
| WO | 2014/150011 A2 | 12/2007 |
| WO | WO 2007/150011 A2 | 12/2007 |

OTHER PUBLICATIONS

U.S. Appl. No. 16/818,368, filed Mar. 13, 2020, Chen et al.
Third Party Observation for Application No. EP20180857375 (Publication No. EP3682884), submitted Jan. 11, 2021, and published on EP Register Jan. 22, 2021.
U.S. Appl. No. 16/455,106, filed Jun. 27, 2019.
Kakkar, et al. Drug Development and Industrial Pharmacy, 23(11): 1063-1067 (1997).
Cayman Chemical Product Guide for Daprodustat (1 page). Retrieved from the Internet at Cayman Chemical—www.caymanchem.com on Jun. 26, 2020 (2016).
Wang, et al. Recent progress of hypoxia inducible factor-prolyl hydroxylase domain containing enzymes inhibitors. J. Int. Pharm. Res., 43(2): 249-59 (Apr. 2016).
International Search Report and Written Opinion for Application No. PCT/CN2018/078766, dated Jun. 20, 2018, 10 pages.
Daprodustat et al., *J. Int. Pharm. Res.*, 43(2):249-259 (2016).
Daprodustat, *Product Information 19915*, (2016).
*Journal of Human Environmental Engineering*, 4:310-317 (2002).
Notification No. 568 of Evaluation and Licensing Division, *Pharmaceutical and Medical Safety Bureau*, MHLW, Japan, (2001).
*Pharm. Stage*, 6(10): 48-53 (2007).
*Pharm. Stage*, 6:20-25 (2007).
*Journal of Synthetic Chemistry*, 65:907-913 (2007).
*Pharmaceutical Research*, 12:945-954 (1995).
*Journal of Human Environmental Engineering*, 4:310-317 (2002). Ref. 4 (Japanese).
Notification No. 568 of Evaluation and Licensing Division, *Pharmaceutical and Medical Safety Bureau, MHLW*, Japan, (2001). Ref. 5 (Japanese).
*Pharm. Stage*, 6: 48-53 (2007). Ref. 6 (Japanese).
*Pharm. Stage*, 6: 20-25 (2007). Ref. 7 (Japanese).
*Journal of Synthetic Organic Chemistry*, Japan, 65:907-913 (2007). Ref. 8 (Japanese).
English Translation of pp. 310-311 Kawaguchi, et al., *Journal of Human Environmental Engineering*, 4:310-317 (2002), Ref. 4.
English Translation of 3.3.1 New Drug Substances, (c) Polymorphic forms, Notification No. 568 of Evaluation and Licensing Division, *Pharmaceutical and Medical Safety Bureau, MHLW*, Japan, (2001), Ref. 5.
English Translation of p. 48 Oshima, Crystallization of Polymorphs and Pseudo-polymorphs and Its Control, *Pharm. Stage*, 6(10): 48-53 (2007), Ref. 6.
English Translation of p. 20 Takata, API form screening and selection in drug discovery stage, *Pharm. Stage*, 6(10): 20-25 (2007), Ref. 7.
English Translation of p. 907 Yamano, Approach to Crystal Polymorph in Process Research of New Drug, *Journal of Synthetic Organic Chemistry*, Japan, 65(9):907-913 (2007), Ref. 8.

* cited by examiner

*Primary Examiner* — Paul V Ward
(74) *Attorney, Agent, or Firm* — Nora L. Stein

(57) ABSTRACT

The present disclosure relates to crystalline form CS1 and CS9 of a hypoxia-inducible factor prolyl hydroxylase inhibitor compound (I) GSK1278863, processes for preparation, and uses for preparing drugs treating and/or preventing anemia thereof.

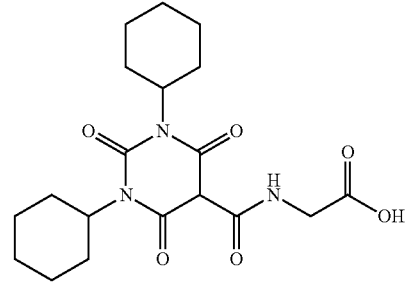

Compound (I)

18 Claims, 19 Drawing Sheets

CRYSTALLINE FORMS OF GSK1278863, PREPARATION METHOD AND PHARMACEUTICAL USE THEREOF

TECHNICAL FIELD

The present disclosure relates to the field of pharmaceutical chemistry, particularly relates to novel crystalline forms of a hypoxia-inducible factor prolyl hydroxylase inhibitor, processes for preparation and use thereof.

BACKGROUND

GSK1278863 (Daprodustat) is an oral hypoxia-inducible factor prolyl hydroxylase inhibitor developed by GlaxoSmithKline for the treatment of anemias, such as chronic kidney disease related anemia.

Currently, the standard treatment for chronic kidney disease-related anemia is injection of recombinant human erythropoietin. However, injecting macromolecular recombinant human erythropoietin is often associated with cardiovascular safety issues. GSK1278863 is a small molecular oral hypoxia-inducible factor prolyl hydroxylase inhibitor. Inhibition of prolyl hydroxylase enzymes promotes the production of red blood cells. The red blood cells can carry oxygen to where the body needs, so as to achieve the purpose of relieving anemia. The mechanism of GSK1278863 is similar to the physiological effects that occur in the body at high altitudes. In clinical, GSK1278863 shows good efficacy and safety in relieving anemia. Compared with recombinant human erythropoietin GSK1278863 can achieve the same efficacy and higher safety. In addition, the oral dosage form of GSK1278863 makes it more convenient for patients to take compared with the injection of macromolecular recombinant human erythropoietin.

The chemical name of GSK1278863 is N-[(1,3-dicyclohexylhexahydro-2,4,6-trioxo-5-pyrimidinyl)carbonyl]-glycine (hereinafter referred to as "Compound (I)"), and the structure is shown as follows:

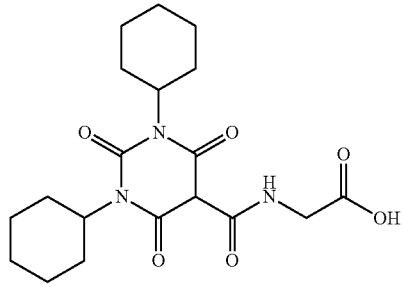

Compound (I)

In the field of pharmaceutical research, different crystalline forms of drug substances have different colors, melting points, solubility, dissolution profiles, chemical stabilities, mechanical stabilities, etc. These properties can affect the quality, safety and efficacy of drug products, which leads to differences in clinical efficacy. Therefore, the research and control of crystalline forms of drug substances have become an important part in drug development.

So far, no crystal form of GSK1278863 has been disclosed. CN101505752B disclosed the chemical structure and preparation method of GSK1278863. The inventors of the present disclosure repeated the method and obtained a solid of GSK1278863. The obtained solid has low purity, extremely high impurity content and high hygroscopicity, which is not suitable for medicine. The inventors of the present disclosure discovered the crystalline form CS1 and form CS9 of GSK1278863 which show excellent performances. Compared to the prior art solid, the crystalline form CS1 and form CS9 of GSK1278863 of the present disclosure have higher purity and lower hygroscopicity. In addition, the crystalline form CS1 and form CS9 provided by the present disclosure have advantages in stability, degradability, solubility, flowability, and in vitro dissolution in formulations, which provides a better choice for the preparation of drug products containing GSK1278863 and is of great significance for drug development.

SUMMARY

The main objective of the present disclosure is to provide novel crystalline forms of GSK1278863, processes for preparation and use thereof.

According to the objective of the present disclosure, crystalline form CS1 of Compound (I) is provided (hereinafter referred to as Form CS1).

The X-ray powder diffraction pattern of Form CS1 shows characteristic peaks at 2theta values of 6.4°±0.2°, 7.5°±0.2° and 7.9°±0.2° using CuKα radiation.

Furthermore, the X-ray powder diffraction pattern of Form CS1 shows one or more characteristic peaks at 2theta values of 17.2°±0.2°, 21.0°±0.2°, 24.0°±0.2° and 19.3°±0.2°. Preferably, the X-ray powder diffraction pattern of Form CS1 shows characteristic peaks at 2theta values of 17.2°±0.2°, 21.0°±0.2°, 24.0°±0.2° and 19.3°±0.2°.

In a preferred embodiment, the X-ray powder diffraction pattern of Form CS1 shows characteristic peaks at 2theta values of 6.4°±0.2°, 7.5°±0.2°, 7.9°±0.2°, 17.2°±0.2°, 21.0°±0.2°, 24.0°±0.2°, and 19.3°±0.2° using CuKα radiation.

Without any limitation being implied, in a specific example of the present disclosure, the X-ray powder diffraction pattern of Form CS1 is substantially as depicted in FIG. 1.

According to the objective of the present disclosure, a process for preparing Form CS1 is also provided. The process comprises:

(1) Dissolving GSK1278863 into a solvent selected from the group consisting of cyclic ethers and ketones, evaporating the obtained solution at 10-50° C. for crystallization; or (2) Dissolving GSK1278863 into a solvent of cyclic ethers, adding an anti-solvent for crystallization, separating and drying to obtain Form CS1.

Furthermore, in method (1), said cyclic ether is preferably tetrahydrofuran; said ketone is preferably acetone, methyl isobutyl ketone or mixtures thereof; said evaporation temperature is preferably room temperature or 50° C.

Furthermore, in method (1), said ketone is more preferably acetone or methyl isobutyl ketone.

Furthermore, in method (2), said cyclic ether is preferably 1, 4-dioxane; said anti-solvent is preferably water; said crystallization time is 0.5-24 h.

Furthermore, in method (2), said crystallization time is preferably 2 h.

According to the objective of the present disclosure, crystalline form CS9 of Compound (I) is provided (hereinafter referred to as Form CS9).

The X-ray powder diffraction pattern of Form CS9 shows characteristic peaks at 2theta values of 4.6°±0.2°, 6.6°±0.2° and 21.1°±0.2° using CuKα radiation.

Furthermore, the X-ray powder diffraction pattern of Form CS9 shows one or more characteristic peaks at 2theta values of 9.4°±0.2°, 20.2°±0.2° and 24.2°±0.2°. Preferably, the X-ray powder diffraction pattern of Form CS9 shows characteristic peaks at 2theta values of 9.4°±0.2°, 20.2°±0.2° and 24.2°±0.2°.

In a preferred embodiment, the X-ray powder diffraction pattern of Form CS9 shows characteristic peaks at 2theta values of 4.6°±0.2°, 6.6°±0.2°, 21.1°±0.2°, 9.4°±0.2°, 20.2°±0.2° and 24.2°±0.2° using CuKα radiation.

Without any limitation being implied, in a specific example of the present disclosure, the X-ray powder diffraction pattern of Form CS9 is substantially as depicted in FIG. 6.

According to the objective of the present disclosure, a process for preparing Form CS9 is also provided. The process comprises:

(1) Dissolving GSK1278863 into a solvent of ethers and adding polymer, evaporating the solution at 10-70° C. for crystallization; or (2) Dissolving GSK1278863 into a solvent mixture of esters and alcohols, and evaporating the solution at 10-70° C. for crystallization.

Furthermore, in method (1), said ethers is preferably methyl tert-butyl ether; said polymer is preferably composed of polycaprolactone, polyoxyethylene, polymethyl methacrylate, hydroxyethyl cellulose, and sodium alginate of equal mass; said evaporation temperature is preferably 50° C.;

Furthermore, in method (2), said ester is preferably ethyl acetate; said alcohol is preferably ethanol; said volume ratio of ester and alcohol is 1:10-10:1; said evaporation temperature is preferably 50° C.

Furthermore, in method (2), said volume ratio of ester and alcohol is preferably 1:1.

In the process for preparing Form CS1 and Form CS9 of the present disclosure:

Said "room temperature" is not a specific value, and refers to 10-30° C.

According to the present disclosure, GSK1278863 as a raw material is solid (crystalline and amorphous), semisolid, wax or oil. Preferably, said compound (I) as a raw material is a solid powder.

In the present disclosure, "crystal" or "crystalline form" refers to the solid being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CS1 and Form CS9 of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the number and the number range should not be understood as the number or number range themselves only. It should be understood by those skilled in the art that the specific number can be shifted at specific technical environment without departing from the spirit and principle of the present disclosure. In the present disclosure, the number of shift ranges expected by one of skilled in the art is represented by the term "about".

Crystalline forms of the present disclosure also have the following advantages:

(1) Compared with the prior art, crystalline forms of the present disclosure have lower hygroscopicity. The weight gain of the prior art solid at 80% RH is 1.14%. The weight gains of Form CS1 and Form CS9 at 80% RH are 0.53% and 0.22%, respectively, which indicates that Form CS1 and Form CS9 can hardly absorb water and gain weight. Form CS1 and Form CS9 are stable under high humidity conditions, which is conducive to long-term storage of drug substances and preparation of drug products;

(2) Compared with prior art, crystalline forms of the present disclosure have higher purity. The purity of the prior art solid is 81.06%, and the impurity content is high. In a specific embodiment, the purity of crystalline forms of the present disclosure is higher than 99%. In another specific embodiment, the purity of crystalline forms of the present disclosure is higher than 99.5%;

(3) Form CS1 and Form CS9 of the present disclosure have good stability. The crystalline of Form CS1 and Form CS9 drug substance doesn't change for at least 3 months when stored under the conditions of 25° C./60% RH, 40° C./75% RH and 60° C./75% RH. The chemical purity remains substantially unchanged during storage. After Form CS1 and Form CS9 are mixed with the excipients to form drug products, and stored under the condition of 40° C./75% RH, the crystalline form of Form CS1 and Form CS9 in the drug products doesn't change for at least 1 months. Crystalline forms of the present disclosure has good stability, ensuring consistent and controllable quality of the drug substance and drug products, which is of great significance for ensuring the efficacy and safety of drugs, avoiding the toxicity caused by impurities, and preventing the occurrence of adverse drug reactions;

(4) The crystalline forms of the present disclosure have good solubility in simulated biological media and pure water, ensuring good dissolution of the crystalline drug substance in drug products. Higher solubility is beneficial to the effective absorption of active ingredients in the drug products in the human body, so as to achieve the ideal drug bioavailability and efficacy.

(5) After being made into tablet formulation, the crystalline forms of the present invention have good dissolution and dissolution rate. In pH=6.8 phosphate buffer solution, the average dissolution at 10 minutes is up to 67.7%, and the average dissolution at 60 minutes is up to 95.2%. Good in vitro dissolution is conducive to increasing the degree of drug absorption and ensure better in vivo exposure, thereby improving drug's bioavailability and efficacy. High dissolution rate is beneficial for the drug to achieve peak concentration in plasma quickly after administration, thus ensuring rapid drug action.

Furthermore, a pharmaceutical composition is provided, said pharmaceutical composition comprises a therapeutically effective amount of Form CS1 or Form CS9 or combinations thereof and pharmaceutically acceptable carriers, diluents or excipients.

Furthermore, Form CS1 or Form CS9 or combinations thereof for the use in preparing hypoxia-inducible factor prolyl hydroxylase inhibitor drugs.

Furthermore, Form CS1 or Form CS9 or combinations thereof can be used for preparing drugs treating and/or preventing anemia.

DETAILED DESCRIPTION

Figure 1:
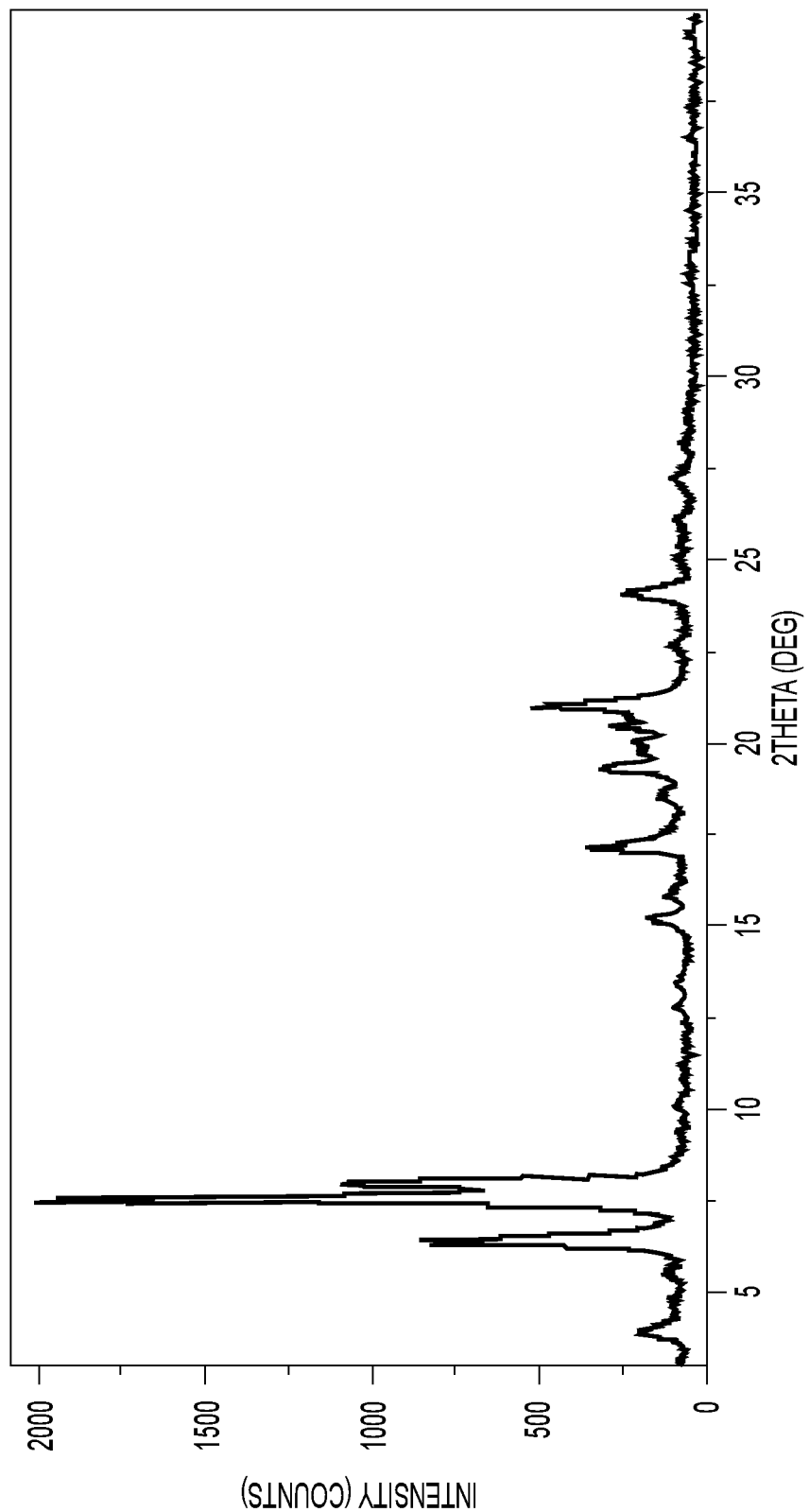
FIG. 1 shows an XRPD pattern of Form CS1 according to example 1.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:
    XRPD: X-ray Powder Diffraction
    DSC: Differential Scanning calorimetry
    TGA: Thermal Gravimetric Analysis
    $^1$H NMR: Proton Nuclear Magnetic Resonance
    DMSO: Dimethyl sulfoxide Instruments and Methods Used for Data Collection X-ray powder diffraction patterns in the present disclosure were acquired by a Panalytical Empyrean X-ray powder diffractometer. The parameters of the X-ray powder diffraction method of the present disclosure were as follows:
    X-ray Reflection: Cu, Kα
    Kα1 (Å): 1.540598; Kα2 (Å): 1.544426
    Kα2/Kα1 intensity ratio: 0.50
    Voltage: 45 (kV)
    Current: 40 (mA)
    Scan range: from 3.0 degree to 40.0 degree Differential scanning calorimetry (DSC) data in the present disclosure were acquired by a TA Q2000. The parameters of the DSC method of the present disclosure were as follows:
    Heating rate: 10° C./min
    Purge gas: nitrogen Thermal gravimetric analysis (TGA) data in the present disclosure were acquired by a TA Q500. The parameters of the TGA method of the present disclosure were as follows:
    Heating rate: 10° C./min
    Purge gas: nitrogen Proton nuclear magnetic resonance spectrum data (H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

High Performance Liquid Chromatography (HPLC) data of purity test in the present disclosure were collected from an Agilent 1260 with UV Variable Wavelength Detector (VWD). The HPLC method parameters for purity test in the present disclosure are as follows:
    Column: Waters XBridge C8, 150×4.6 mm, 3.5 μm
    Mobile Phase: A: 0.1% TFA in $H_2O$
    B: 0.1% TFA in Acetonitrile
    Gradient:

| Time (min) | % B |
| --- | --- |
| 0.0 | 20 |
| 5.0 | 50 |
| 30.0 | 80 |
| 35.0 | 80 |
| 35.1 | 20 |
| 40.0 | 20 |

Flow rate: 1.0 mL/min
Injection Volume: 34
Column Temperature: 40° C.
Diluent: MeOH High Performance Liquid Chromatography (HPLC) data of solubility test in the present disclosure were collected from an Agilent 1260 with UV Variable Wavelength Detector (VWD). The HPLC method parameters are as follows:

The HPLC method parameters for solubility test in the present disclosure are as follows:

Column: Waters XBridge C8 150×4.6 mm, 5 μm
Mobile Phase: A: 0.1% TFA in $H_2O$
B: 0.1% TFA in Acetonitrile
Gradient:

| Time (min) | % B |
| --- | --- |
| 0.0 | 65 |
| 10.0 | 80 |
| 12.0 | 80 |
| 12.1 | 65 |
| 16.0 | 65 |

Flow rate: 1.1 mL/min
Injection Volume: 5 μL
Column Temperature: 40° C.
Diluent: MeOH Unless otherwise specified, the following examples were conducted at room temperature.

Raw materials of GSK1278863 used in the following examples were prepared by known methods in the prior art, for example, the method disclosed in CN101505752B. The prior art solid in the following examples refer to the solid of GSK1278863 obtained by repeating the preparation method disclosed in CN101505752B.

Example 1~4: Preparation of Form CS1

Example 1

6.4 mg of GSK1278863 was weighed and dissolved in 0.5 mL of tetrahydrofuran. The obtained solution was evaporated at room temperature for about 2 days to precipitate solid. The obtained solid was confirmed to be Form CS1. The XRPD pattern is substantially as depicted in FIG. 1, and the XRPD data are listed in Table 1.

Figure 2:
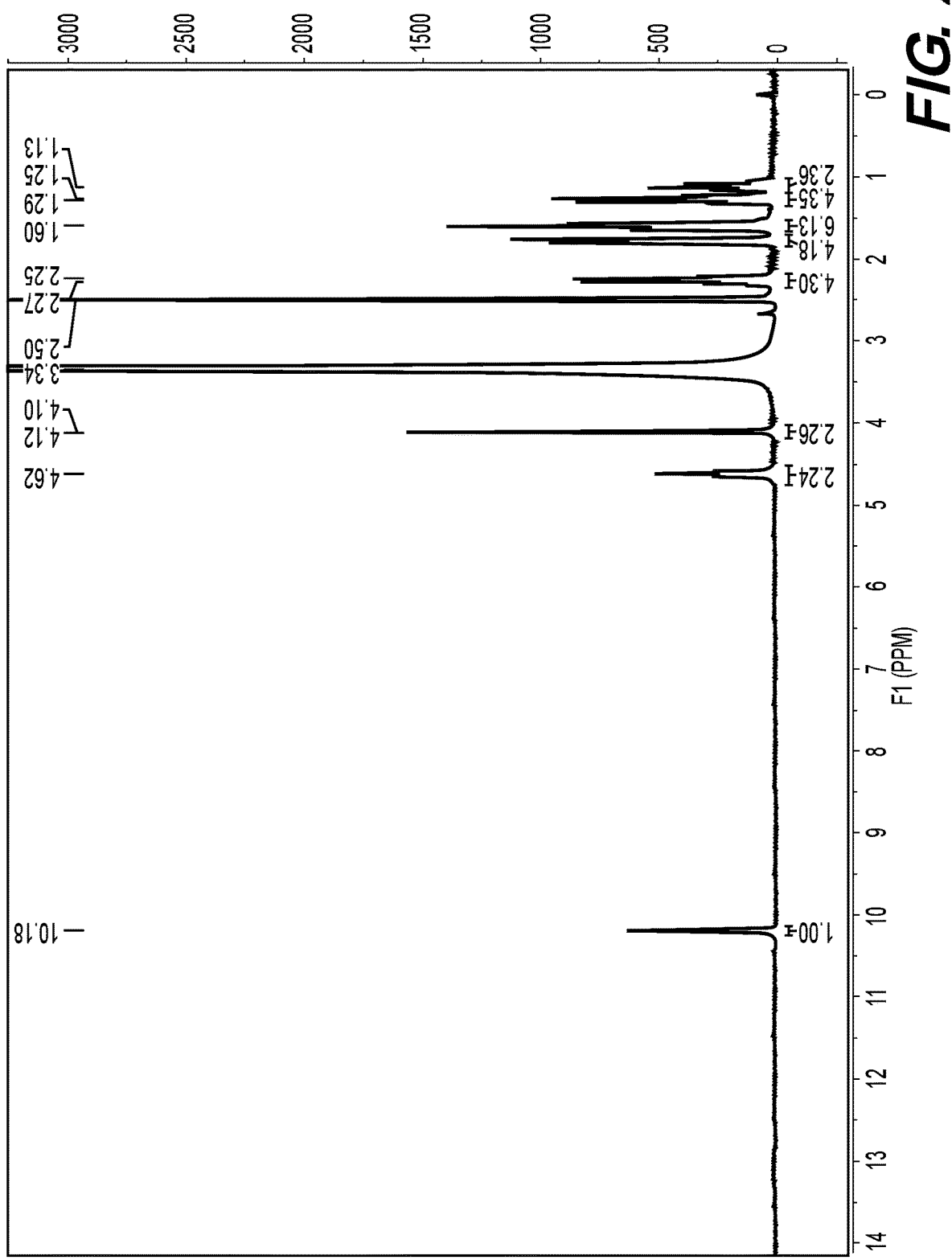
FIG. 2 shows a $^1$H NMR spectrum of Form CS1 according to example 1.

The $^1$H NMR spectrum of Form CS1 is substantially as depicted in FIG. 2, and the corresponding data are: $^1$H NMR (400 MHz, $d_6$-DMSO) δ 10.18 (s, 1H), 4.62 (s, 2H), 4.11 (d, J=5.8 Hz, 2H), 2.26 (d, J=10.9 Hz, 4H), 1.78 (d, J=12.6 Hz, 4H), 1.60 (t, J=11.8 Hz, 6H), 1.27 (d, J=12.9 Hz, 4H), 1.13 (s, 2H).

Figure 3:
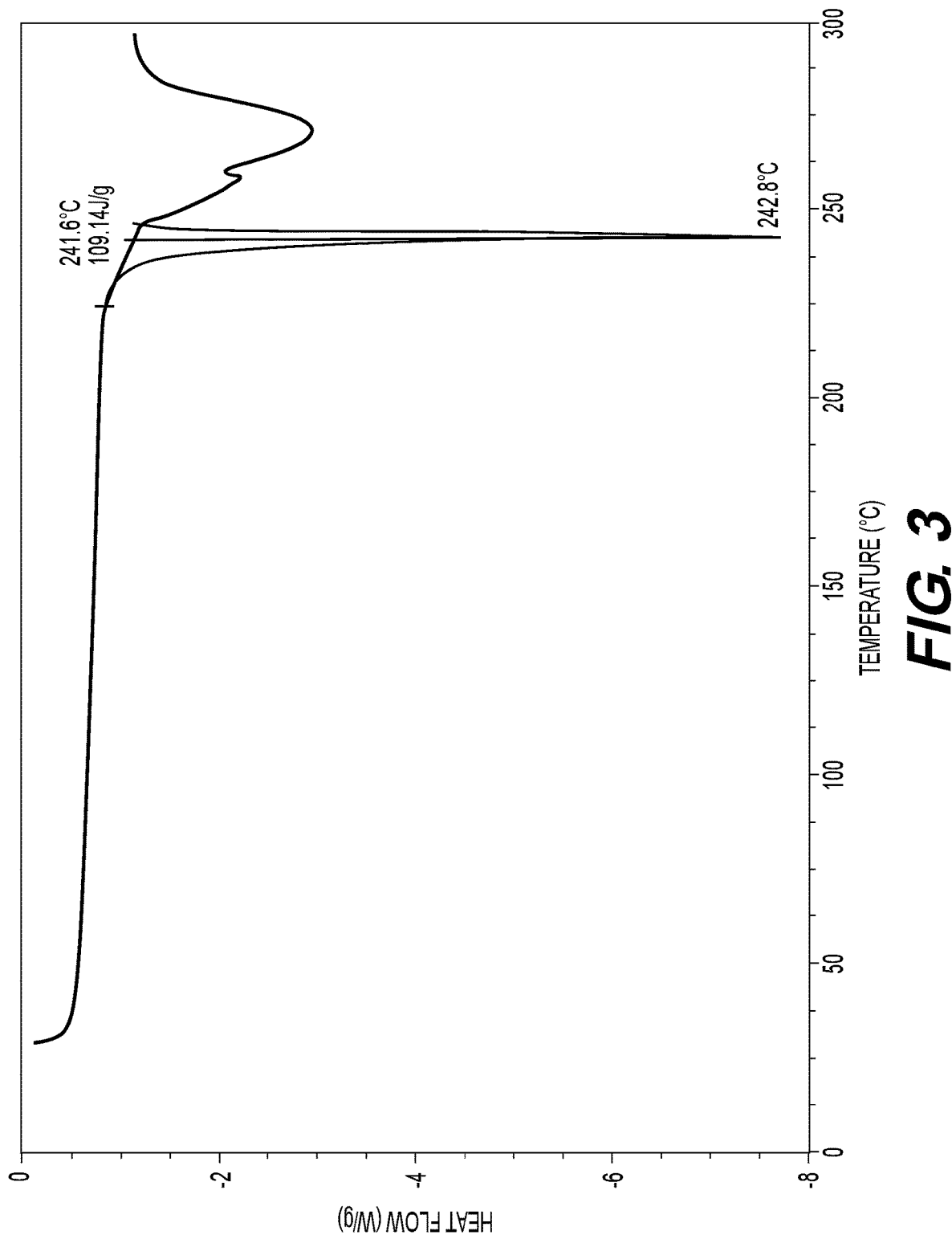
FIG. 3 shows a DSC curve of Form CS1 according to example 1.

The DSC curve of Form CS1 is substantially as depicted in FIG. 3. The endothermic peak at around 242° C. corresponds to the melting endothermic peak of the Form CS1.

Figure 4:
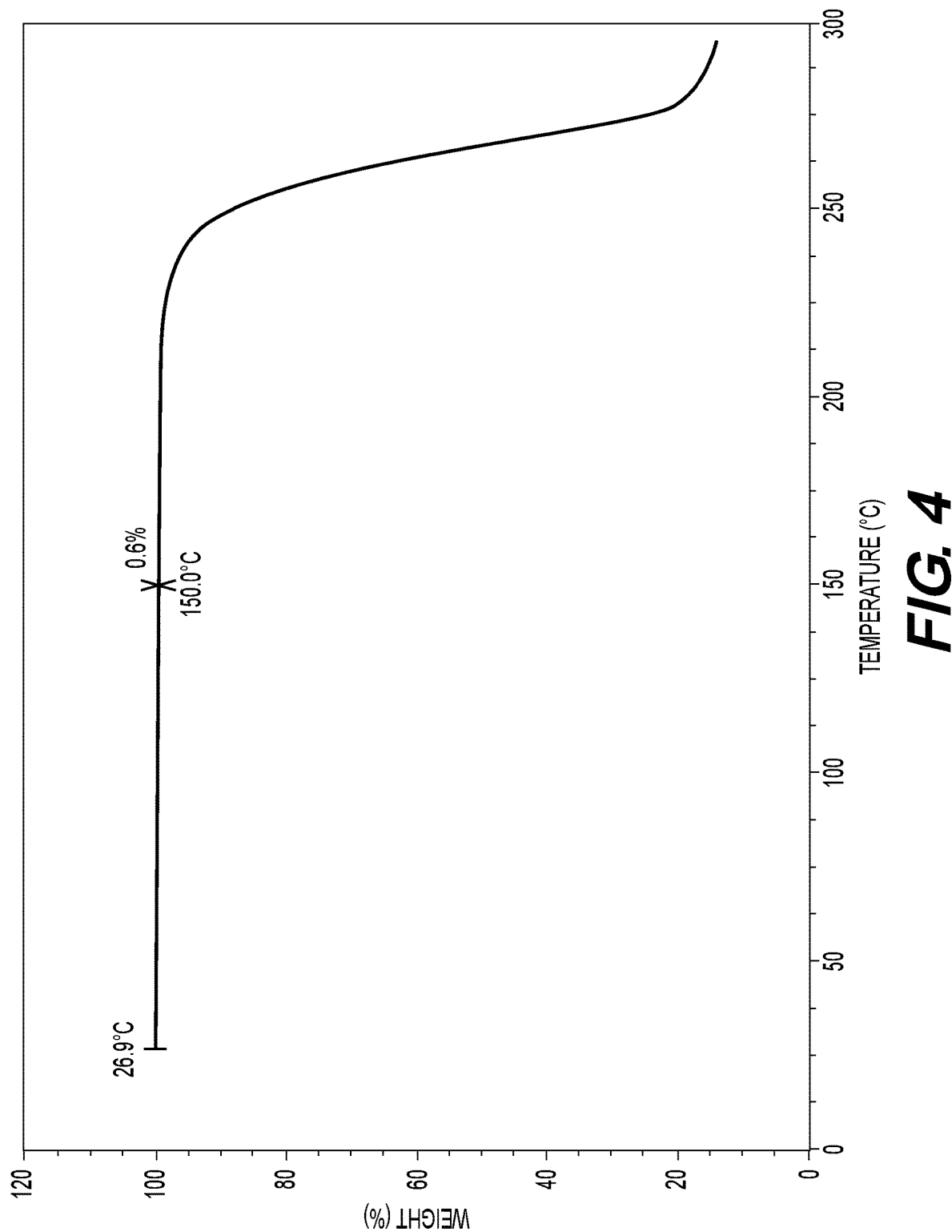
FIG. 4 shows a TGA curve of Form CS1 according to example 1.

The TGA curve of Form CS1 shows about 0.6% weight loss when heated to 150° C., which is substantially as depicted in FIG. 4.

TABLE 1

| Diffraction angle 2θ | d spacing | Intensity % |
| --- | --- | --- |
| 3.94 | 22.44 | 7.43 |
| 5.53 | 15.98 | 3.05 |
| 6.41 | 13.80 | 41.18 |
| 7.51 | 11.77 | 100.00 |

TABLE 1-continued

| Diffraction angle 2θ | d spacing | Intensity % |
| --- | --- | --- |
| 7.94 | 11.14 | 52.84 |
| 10.16 | 8.71 | 1.90 |
| 12.80 | 6.91 | 2.00 |
| 13.47 | 6.57 | 2.08 |
| 15.20 | 5.83 | 5.68 |
| 15.89 | 5.58 | 2.92 |
| 17.15 | 5.17 | 15.13 |
| 18.52 | 4.79 | 3.88 |
| 19.25 | 4.61 | 13.52 |
| 19.92 | 4.46 | 7.60 |
| 20.41 | 4.35 | 11.08 |
| 20.99 | 4.23 | 24.54 |
| 22.60 | 3.93 | 2.29 |
| 24.04 | 3.70 | 10.32 |
| 26.08 | 3.42 | 2.46 |
| 27.19 | 3.28 | 2.23 |
| 32.89 | 2.72 | 0.61 |

Example 2~3

Figure 5:
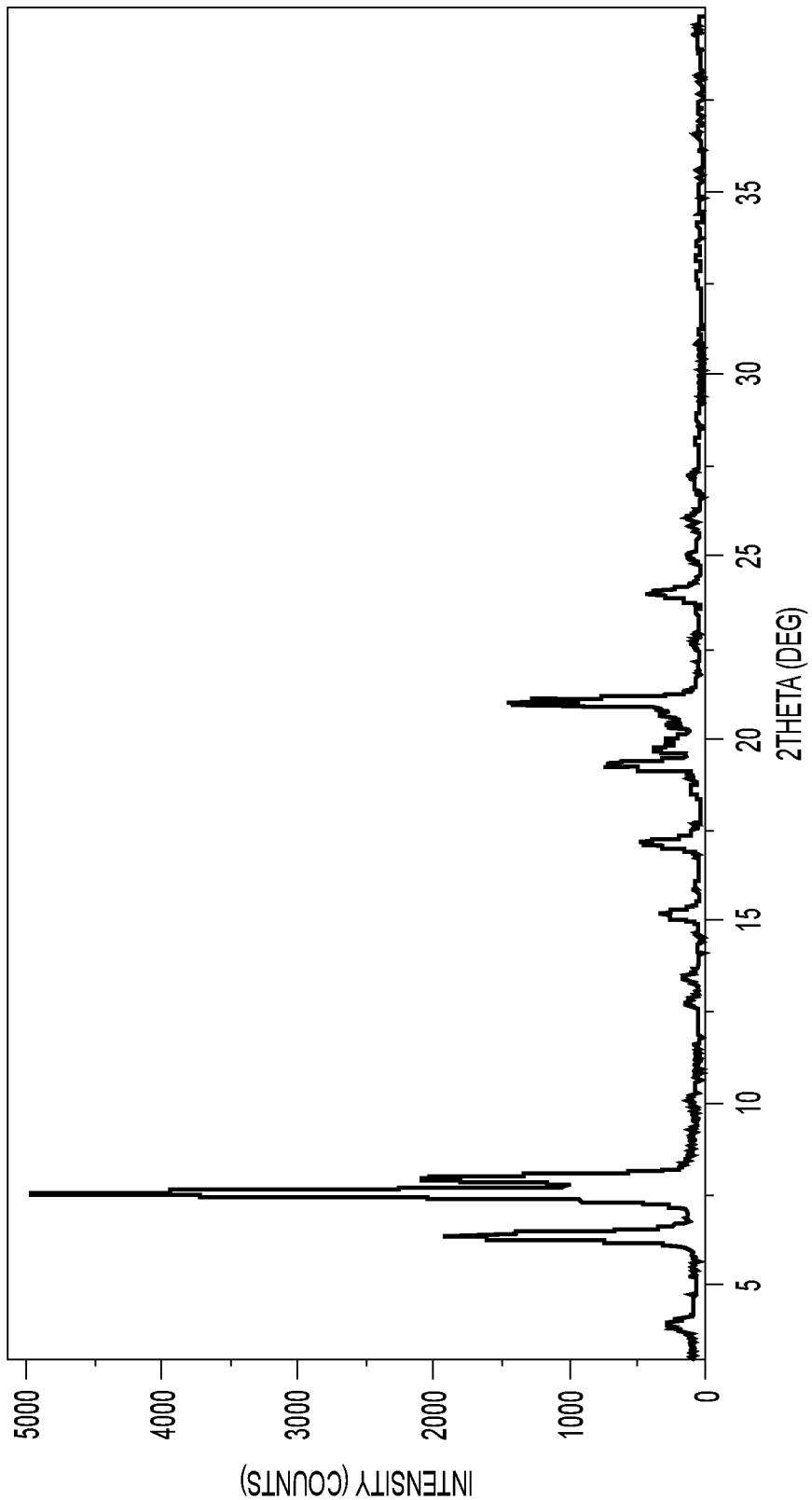
FIG. 5 shows an XRPD pattern of Form CS1 according to example 2.

As shown in Table 2, certain amount of GSK1278863 was weighed and dissolved in corresponding solvents. The obtained solution was evaporated at 50° C. to obtain solid. The solid obtained in example 2 and example 3 was collected and labeled as sample 2 and sample 3. Sample 2 and sample 3 were confirmed to be Form CS1. Sample 2 was selected for tests. The XRPD pattern is substantially as depicted in FIG. 5, and the XRPD data are listed in Table 3.

TABLE 2

| Example | Amount (mg) | Solvent | Volume (mL) | Label |
| --- | --- | --- | --- | --- |
| 2 | 6.7 | Methyl isobutyl ketone | 0.7 | 2 |
| 3 | 6.6 | Acetone | 0.7 | 3 |

TABLE 3

| Diffraction angle 2θ | d spacing | Intensity % |
| --- | --- | --- |
| 3.93 | 22.47 | 5.30 |
| 6.35 | 13.93 | 37.90 |
| 7.53 | 11.75 | 100.00 |
| 7.92 | 11.17 | 41.23 |
| 10.12 | 8.74 | 1.65 |
| 12.80 | 6.92 | 2.37 |
| 13.44 | 6.59 | 2.83 |
| 15.19 | 5.83 | 6.22 |
| 15.92 | 5.57 | 0.81 |
| 17.13 | 5.18 | 8.90 |
| 18.60 | 4.77 | 1.07 |
| 19.27 | 4.61 | 14.44 |
| 19.75 | 4.50 | 7.17 |
| 20.00 | 4.44 | 5.18 |
| 20.41 | 4.35 | 5.27 |
| 21.00 | 4.23 | 28.87 |
| 22.64 | 3.93 | 1.35 |
| 24.02 | 3.71 | 7.91 |
| 25.04 | 3.56 | 1.66 |
| 26.11 | 3.41 | 2.34 |
| 27.24 | 3.27 | 1.55 |
| 28.18 | 3.17 | 0.69 |
| 28.83 | 3.10 | 0.58 |
| 32.76 | 2.73 | 0.86 |
| 36.60 | 2.46 | 0.50 |

Example 4

10.1 mg of GSK1278863 was weighed and dissolved in 0.5 mL of 1, 4-dioxane. Then, 2.0 mL of water was added dropwise as an anti-solvent. The obtained solution was stirred at room temperature for 2 h, centrifuged, and dried under vacuum to obtain crystalline solid. The obtained solid was confirmed to be Form CS1.

Example 5~6: Preparation of Form CS9

Example 5

Figure 6:
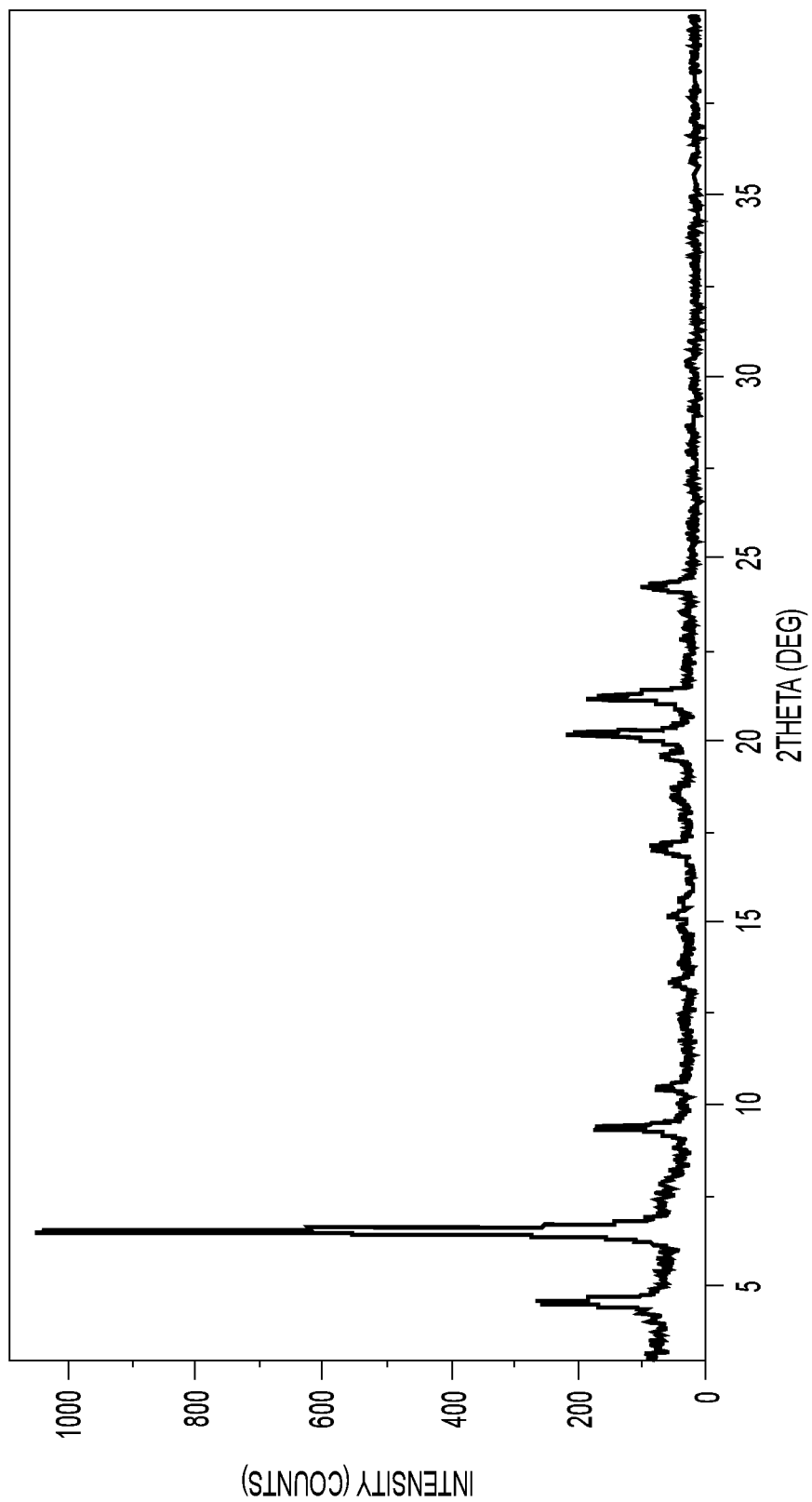
FIG. 6 shows an XRPD pattern of Form CS9 according to example 5.

4.6 mg of GSK1278863 was weighed and dissolved in 0.7 mL methyl tert-butyl ether solvent, followed by adding polymer. The polymer was composed of polycaprolactone, polyoxyethylene, polymethyl methacrylate, hydroxyethyl cellulose, and sodium alginate of equal masses. The solution was evaporated at 50° C. for about 1 day to precipitate solid. The obtained solid was confirmed to be Form CS9. The XRPD pattern is substantially as depicted in FIG. 6, and the XRPD data are listed in Table 4.

Figure 7:
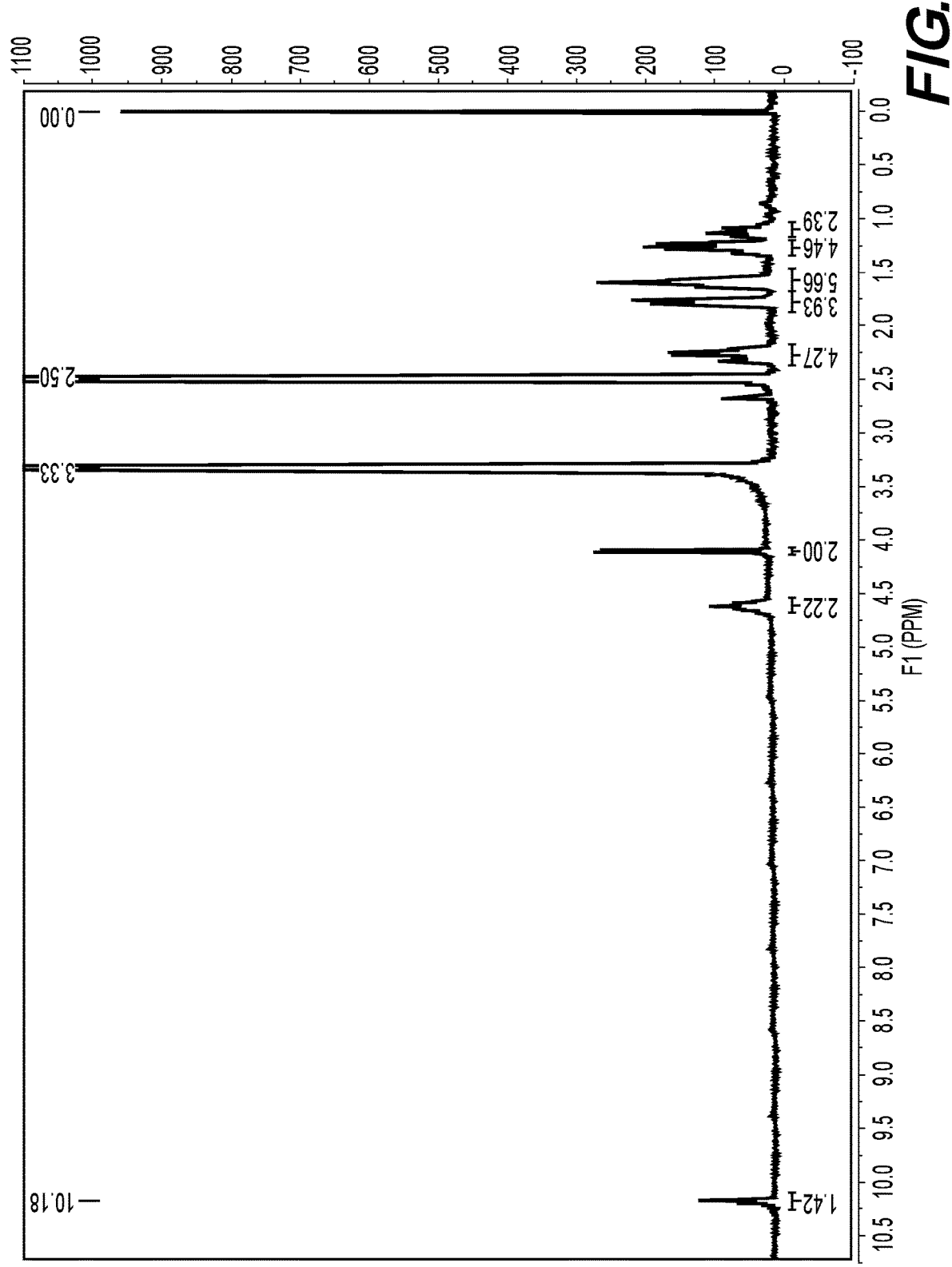
FIG. 7 shows a $^1$H NMR spectrum of Form CS9 according to example 5.

The $^1$H NMR spectrum of Form CS9 is substantially as depicted in FIG. 7, and the corresponding data are: $^1$HNMR (400 MHz, d$_6$-DMSO) δ 10.18 (s, 1H), 4.62 (s, 2H), 4.10 (d, J=5.6 Hz, 2H), 2.36-2.17 (m, 4H), 1.78 (d, J=12.4 Hz, 4H), 1.60 (s, 6H), 1.34-1.21 (m, 4H), 1.11 (d, J=13.1 Hz, 2H).

TABLE 4

| Diffraction angle 2θ | d spacing | Intensity % |
| --- | --- | --- |
| 4.58 | 19.29 | 19.65 |
| 6.56 | 13.47 | 100.00 |
| 9.37 | 9.44 | 13.93 |
| 10.50 | 8.43 | 4.37 |
| 13.34 | 6.64 | 2.86 |
| 15.10 | 5.87 | 1.57 |
| 17.13 | 5.18 | 4.23 |
| 18.51 | 4.79 | 1.99 |
| 19.54 | 4.54 | 4.14 |
| 20.18 | 4.40 | 17.65 |
| 21.14 | 4.20 | 15.46 |
| 24.23 | 3.67 | 7.74 |
| 30.20 | 2.96 | 0.63 |

Example 6

6.9 mg of GSK1278863 raw materials was weighed and dissolved in 0.7 mL of ethyl acetate:ethanol (V/V, 1:1). The obtained solution was evaporated at 50° C. for about 4 days to precipitate solid. The obtained solid was confirmed to be Form CS9.

Figure 8:
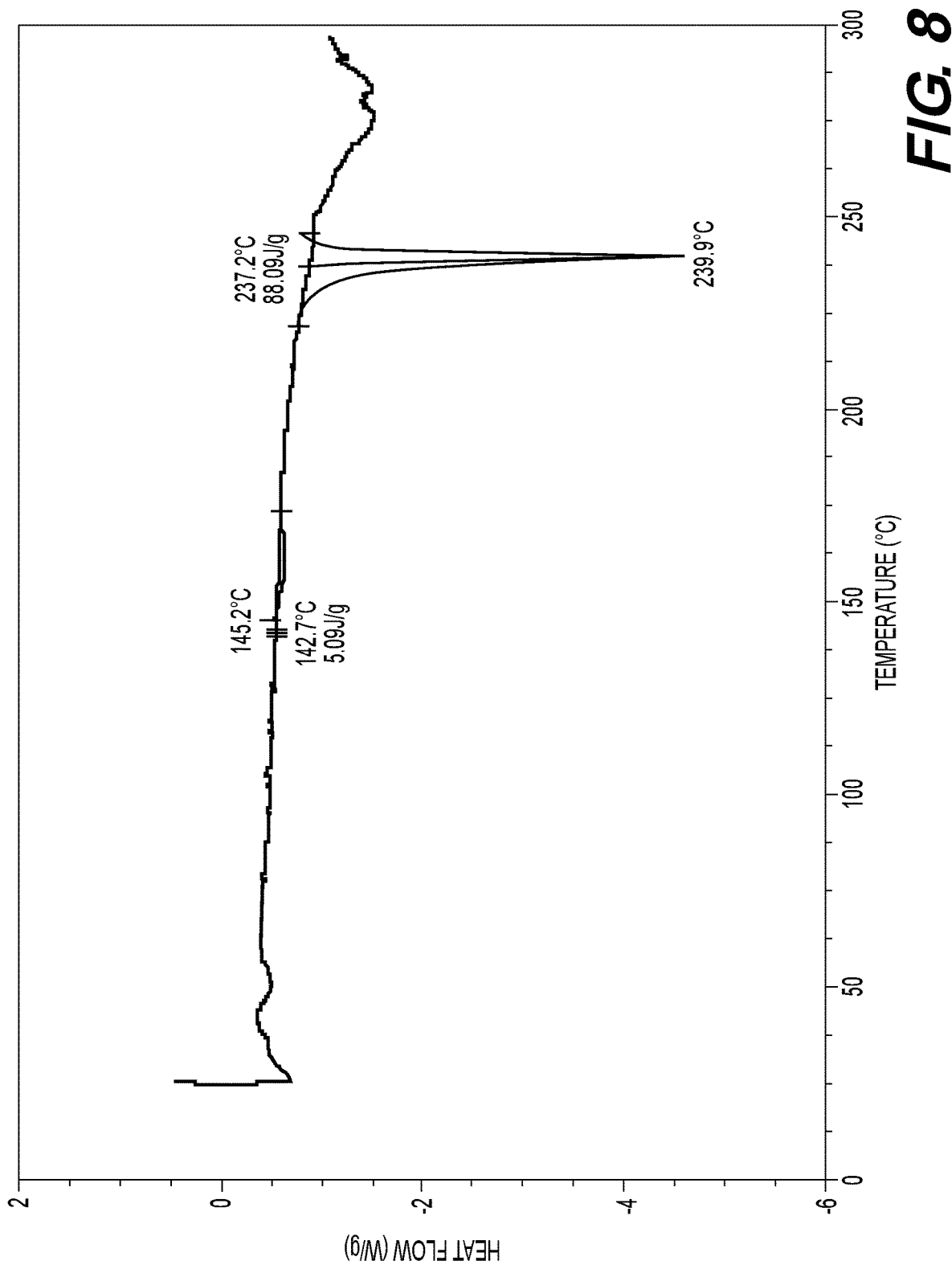
FIG. 8 shows a DSC curve of Form CS9.

The DSC curve of Form CS9 is substantially as depicted in FIG. 8. The first endothermic peak appears when heated to around 145° C. and the second endothermic peak appears when heated to around 237° C.

Figure 9:
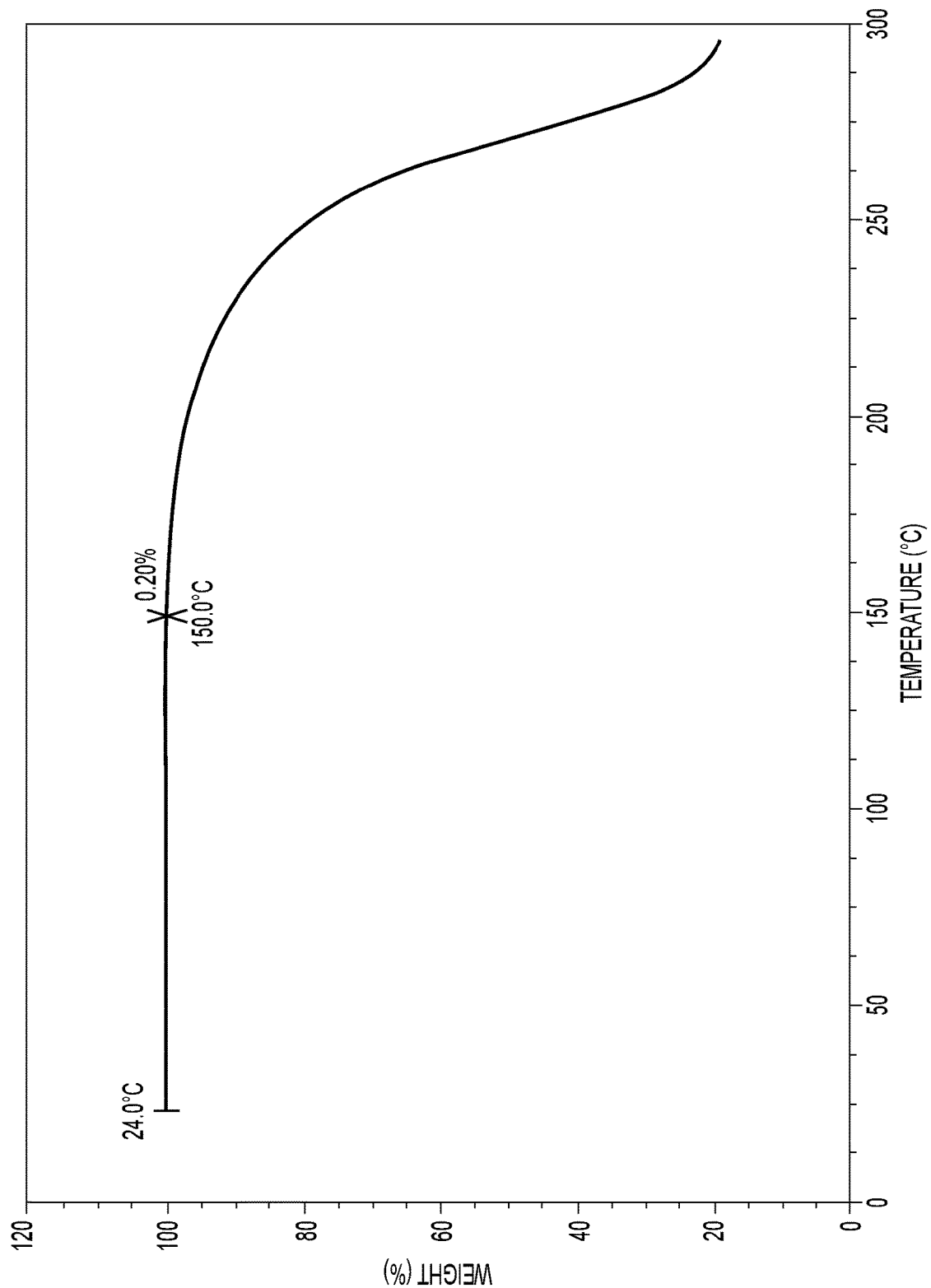
FIG. 9 shows a TGA curve of Form CS9.

The TGA curve of Form CS9 shows about 0.2% weight loss when heated to 150° C., which is substantially as depicted in FIG. 9.

Figure 10:
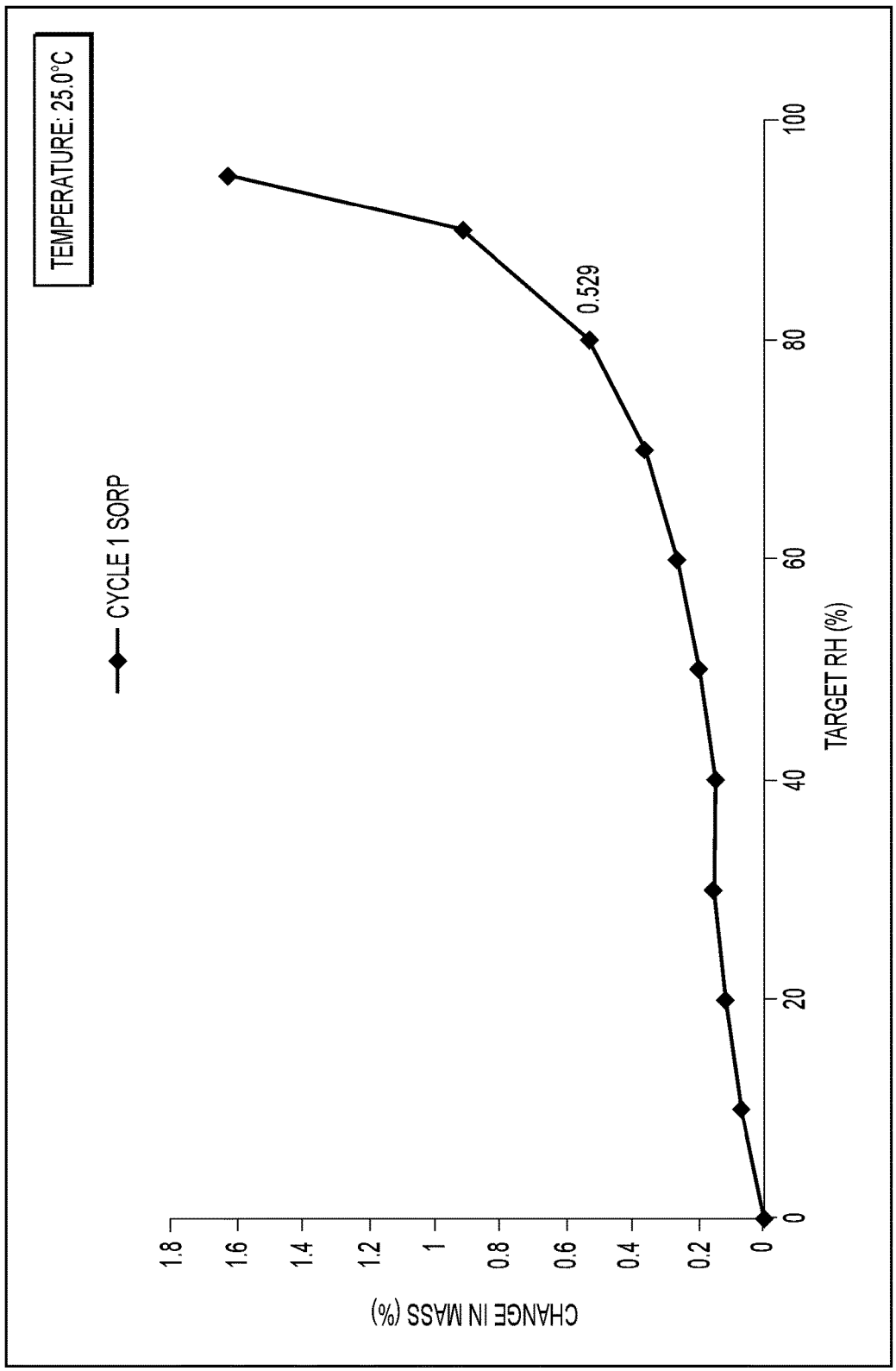
FIG. 10 shows a DVS plot of Form CS1.
Figure 11:
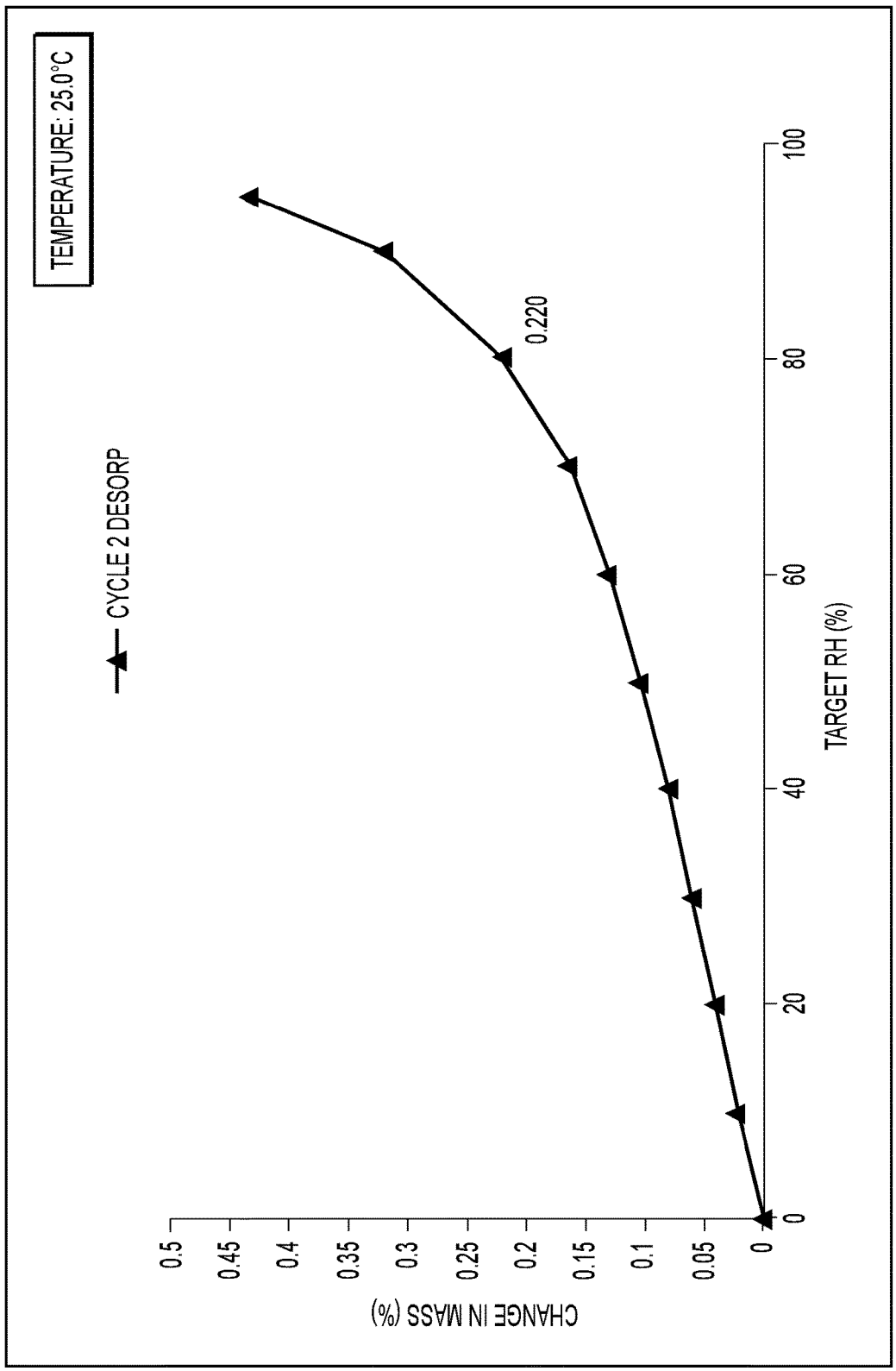
FIG. 11 shows a DVS plot of Form CS9.
Figure 12:
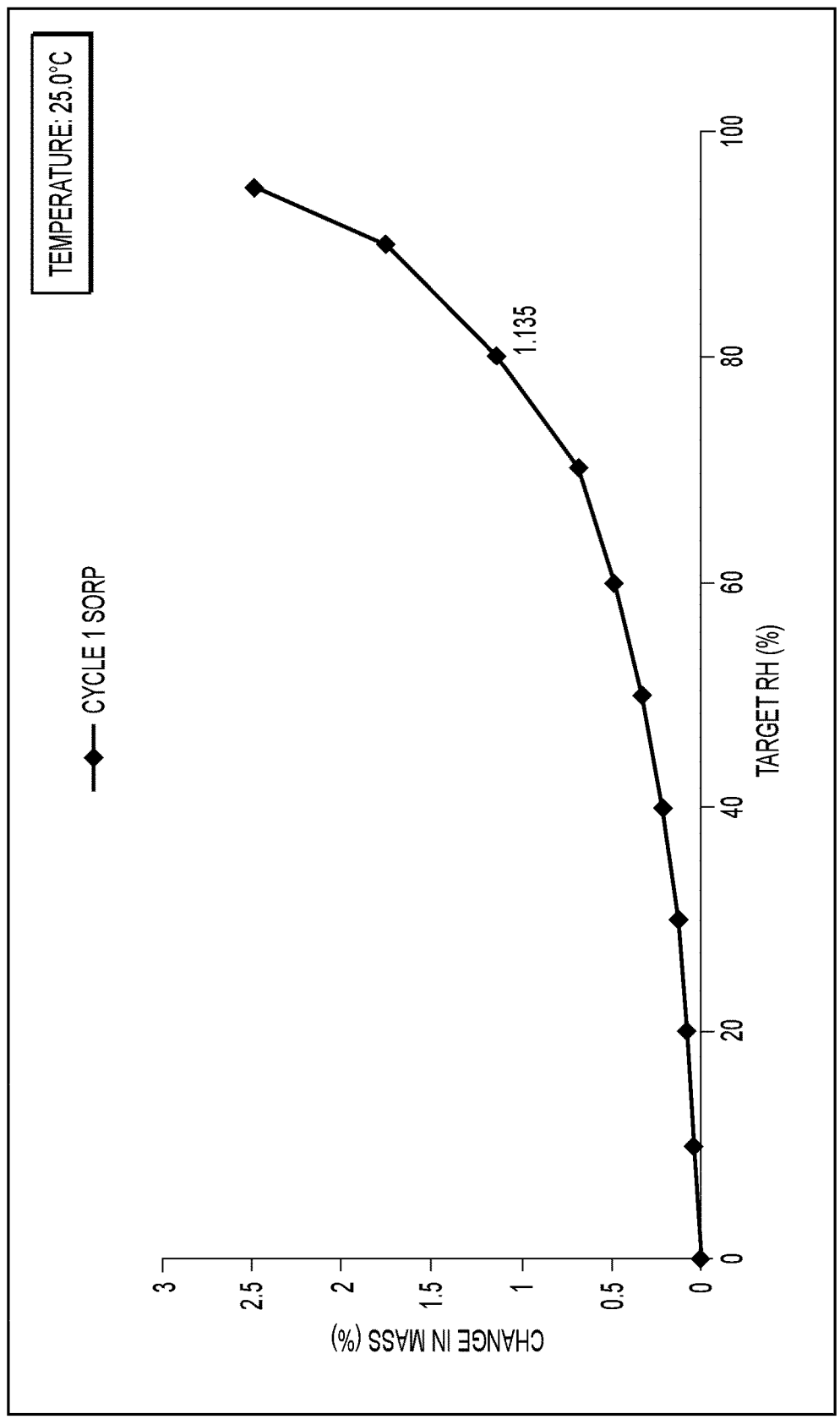
FIG. 12 shows a DVS plot of the solid of the prior art.

Example 7: Hygroscopicity Comparison of Form CS1, Form CS9 and the Prior Art Solid Dynamic vapor sorption (DVS) was applied to test hygroscopicity of Form CS1, Form CS9 and the prior art solid with about 10 mg of samples under 25° C. The results are listed in Table 5. The DVS plots of Form CS1, Form CS9 and the prior art solid are substantially as depicted in FIG. 10, FIG. 11 and FIG. 12.

TABLE 5

Comparison of hygroscopicity

| Form | Weight gain under 80% Relative Humidity |
| --- | --- |
| Form CS1 | 0.53% |
| Form CS9 | 0.22% |
| The prior art solid | 1.14% |

The result indicates that under 25° C./80% RH, Form CS1 and Form CS9 can hardly absorb water and gain weight. Form CS1 and Form CS9 are very stable at high humidity conditions and not hygroscopic. In comparison, the prior art solid shows higher weight gain and higher hygroscopicity under the same conditions.

Crystalline form with low hygroscopicity doesn't require special drying conditions during the preparation process, which simplifies the preparation and post-treatment process of the drug and is easy for industrial production. Form CS1 and Form CS9 of the present disclosure have lower hygroscopicity than the prior art solid, which reduces the requirements of the storage environment. For example, it doesn't require special storage humidity, which reduces the cost and is beneficial for long-term storage of drug substance and drug products.

Example 8: Purity Comparison of Form CS1, Form CS9 and the Prior Art Solid

HPLC was applied to test the chemical purity of Form CS1, Form CS9 and prior art solid. The results are listed in Table 6.

TABLE 6

| Form | Form CS1 | Form CS9 | The prior art solid |
| --- | --- | --- | --- |
| Purity | 99.88% | 99.86% | 81.06% |
| Impurities content | 0.12% | 0.14% | 18.94% |

The purity of the drug substance is important for ensuring the efficacy and safety of the drug products and preventing the adverse drug reactions. The impurity content of the prior art solid is extremely high, up to 18.94%, which will lead to significantly lowered active ingredient content or reduced drug activity. High impurity content will also lead to significantly increased toxicity and side effects of the drug products. Therefore, the prior art solid cannot be used directly in the preparation of drug products.

The crystalline forms of the present disclosure have high purity, which meets the strict requirements for the purity of the drug substance in the formulations, and is suitable for the subsequent formulation preparation and drug production.

Example 9: Stability Assessment of Form CS1

Figure 13:
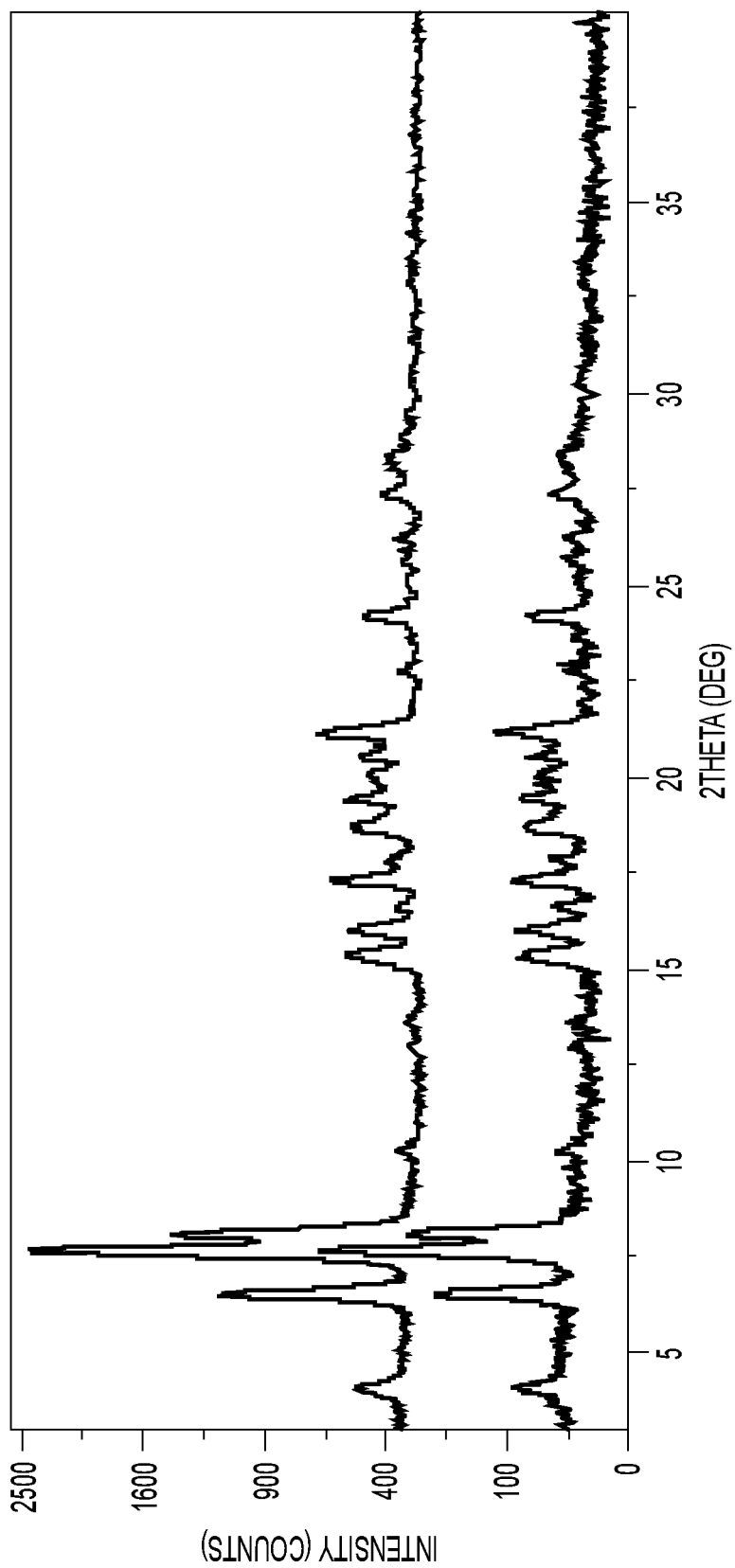
FIG. 13 shows an XRPD pattern overlay of Form CS1 of the present disclosure before and after being stored under 25° C./60% RH for 3 months (from top to bottom: XRPD pattern before storage, XRPD pattern after storage).
Figure 14:
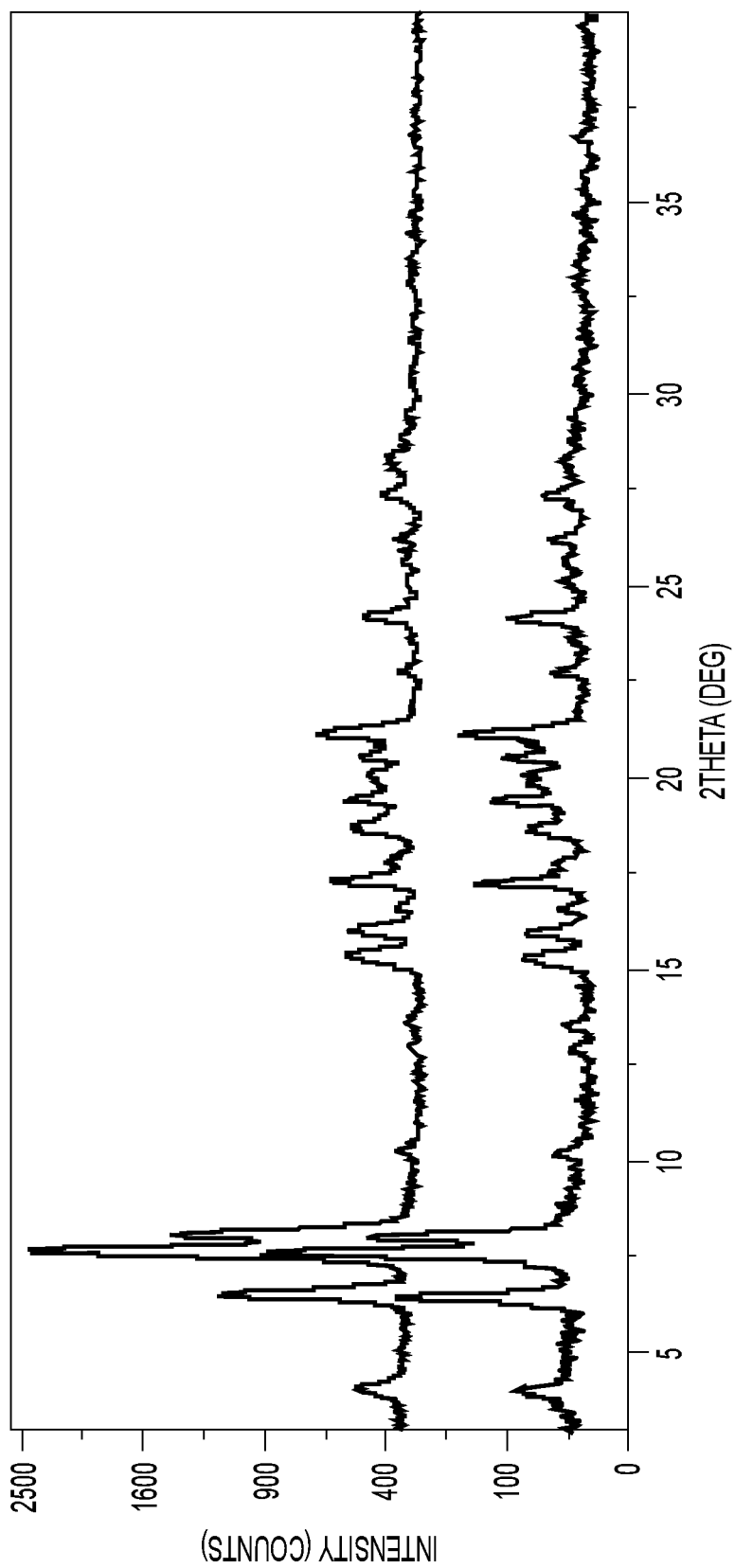
FIG. 14 shows an XRPD pattern overlay of Form CS1 of the present disclosure before and after being stored under 40° C./75% RH for 3 months (from top to bottom: XRPD pattern before storage, XRPD pattern after storage).
Figure 15:
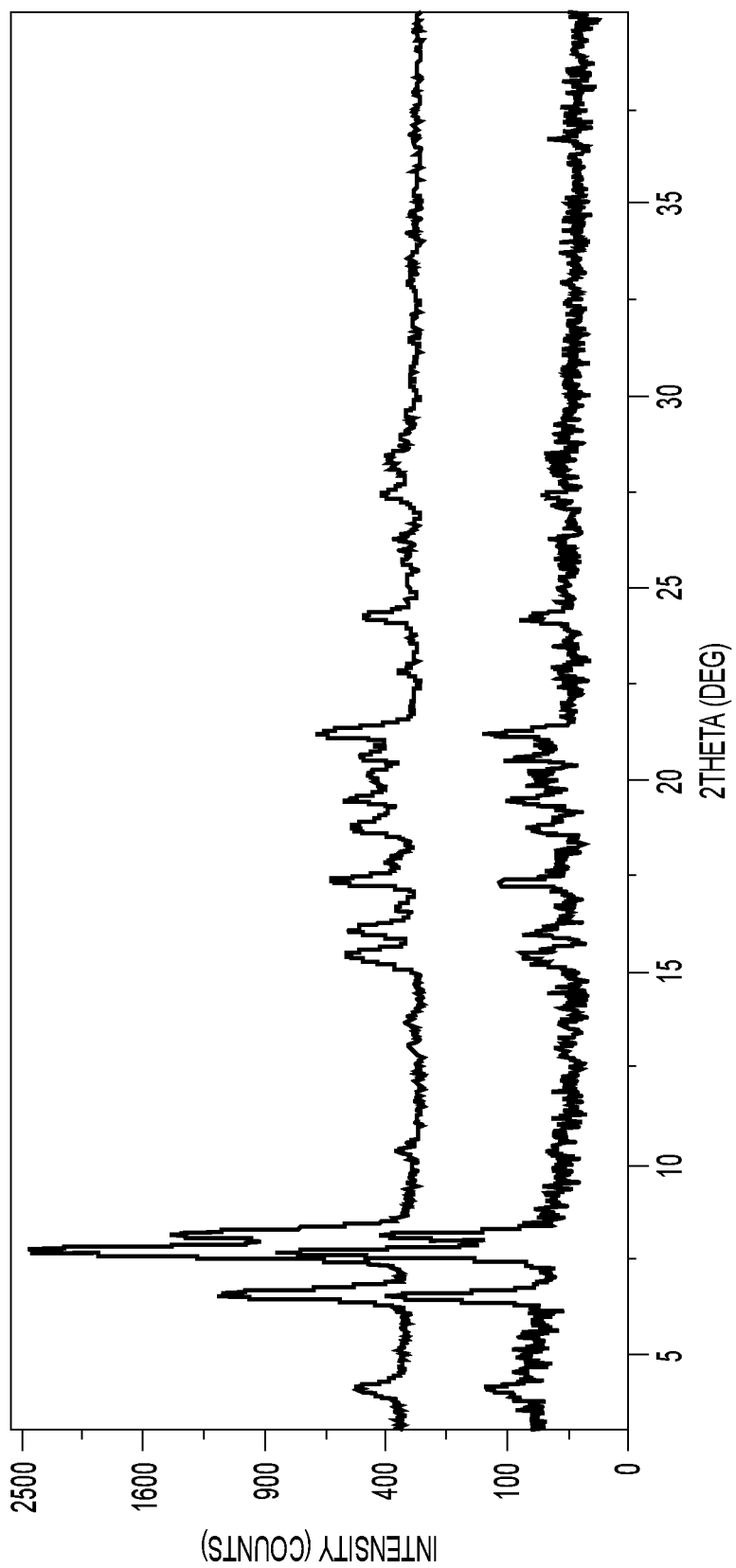
FIG. 15 shows an XRPD pattern overlay of Form CS1 of the present disclosure before and after being stored under 60° C./75% RH for 3 months (from top to bottom: XRPD pattern before storage, XRPD pattern after storage).

Form CS1 was stored under different conditions of 25° C./60% RH, 40° C./75% RH and 60° C./75% RH. The XRPD pattern overlay before and after being stored is substantially as depicted in FIG. 13, FIG. 14 and FIG. 15. The results are shown in Table 7.

TABLE 7

| Initial solid form | Condition | Time | Solid form after storage |
|---|---|---|---|
| Form CS1 (Top of FIG. 13) | 25° C./60% RH | 3 months | Form CS1 (Bottom of FIG. 13) |
| Form CS1 (Top of FIG. 14) | 40° C./75% RH | 3 months | Form CS1 (Bottom of FIG. 14) |
| Form CS1 (Top of FIG. 15) | 60° C./75% RH | 3 months | Form CS1 (Bottom of FIG. 15) |

Furthermore, the inventors also studied the purity change of Form CS1 before and after being stored under the conditions of 25° C./60% RH, 40° C./75% RH and 60° C./75% RH for 3 months, and the results are shown in Table 8.

TABLE 8

| Condition | Initial purity | Purity after 3 months | Purity change |
|---|---|---|---|
| 25° C./60% RH | 99.88% | 99.78% | 0.10% |
| 40° C./75% RH |  | 99.81% | 0.07% |
| 60° C./75% RH |  | 99.81% | 0.07% |

Form CS1 of the present disclosure doesn't change for at least 3 months when stored under the condition of 25° C./60% RH, 40° C./75% RH and 60° C./75% RH, indicating that Form CS1 has good physical stability. The chemical purity remains substantially unchanged during storage, which indicates that Form CS1 does not degrade easily and has good chemical stability.

As active pharmaceutical ingredient plays an important part in drug products, it is vital that the crystalline active pharmaceutical ingredient has good physical and chemical stability. Good physical stability of Form CS1 avoids crystal transformation during the storage and formulation processes, thereby ensuring consistent and controllable quality of the drug substance and drug products.

During the storage of drug products, the purity decrease will result in significantly lower drug substance content and reduced drug activity. The decrease in purity also significantly increase the toxicity and side effects, affecting the efficacy and safety of drug products. Good chemical stability of Form CS1 makes the purity keep basically unchanged during storage, which is of great significance to ensure the efficacy and safety of drugs and prevent the occurrence of adverse drug effects. In addition, stable crystalline form is more controllable in the crystallization process, and less prone to impurities and mixed crystals, which is conducive to industrial production.

The stability of drug products containing Form CS1 can be forecasted from the stability results of Form CS1 drug substance, providing a guarantee for the preparation of stable drug products.

Example 10: Stability Assessment of Form CS9

Figure 16:
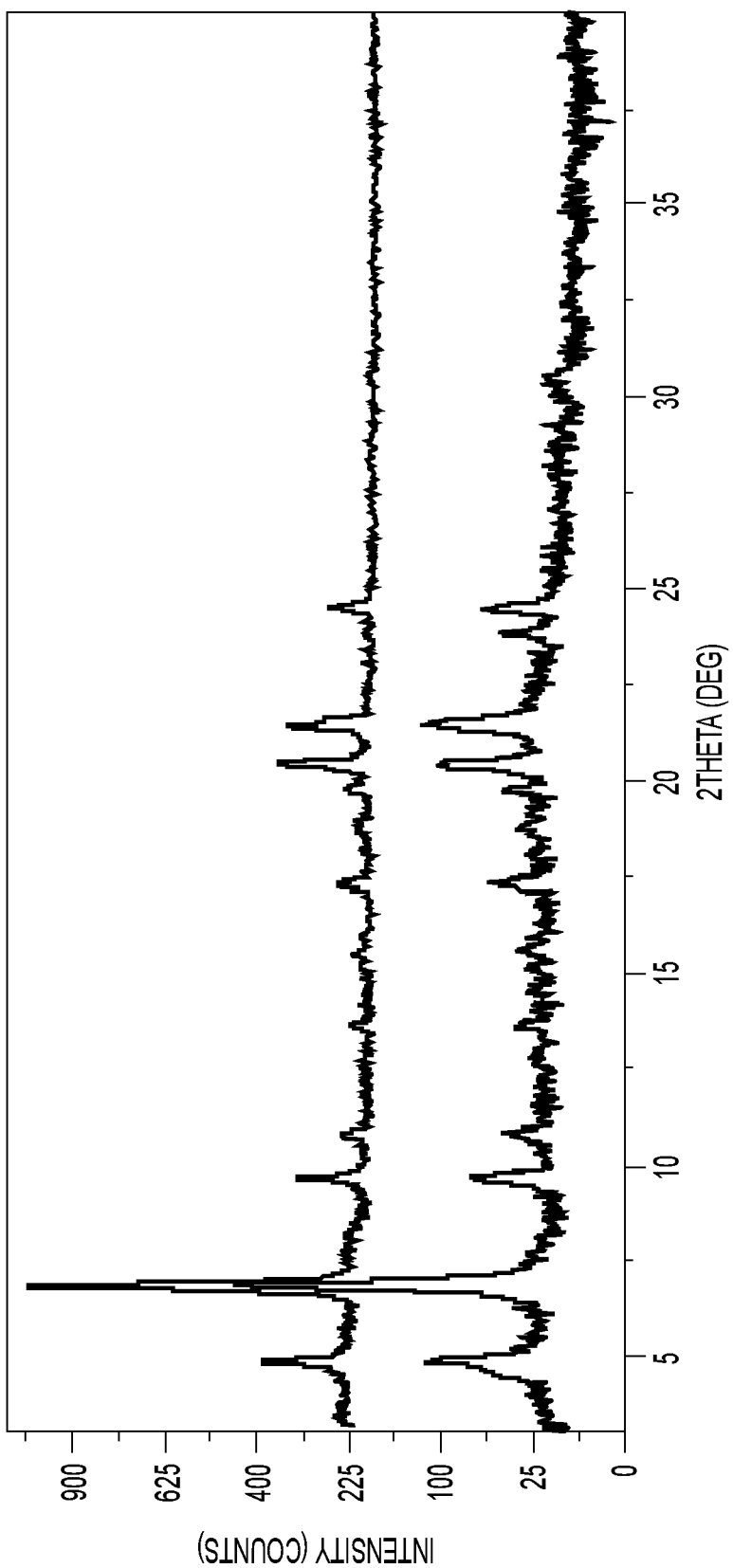
FIG. 16 shows an XRPD pattern overlay of Form CS9 of the present disclosure before and after being stored under 25° C./60% RH for 3 months (from top to bottom: XRPD pattern before storage, XRPD pattern after storage).
Figure 17:
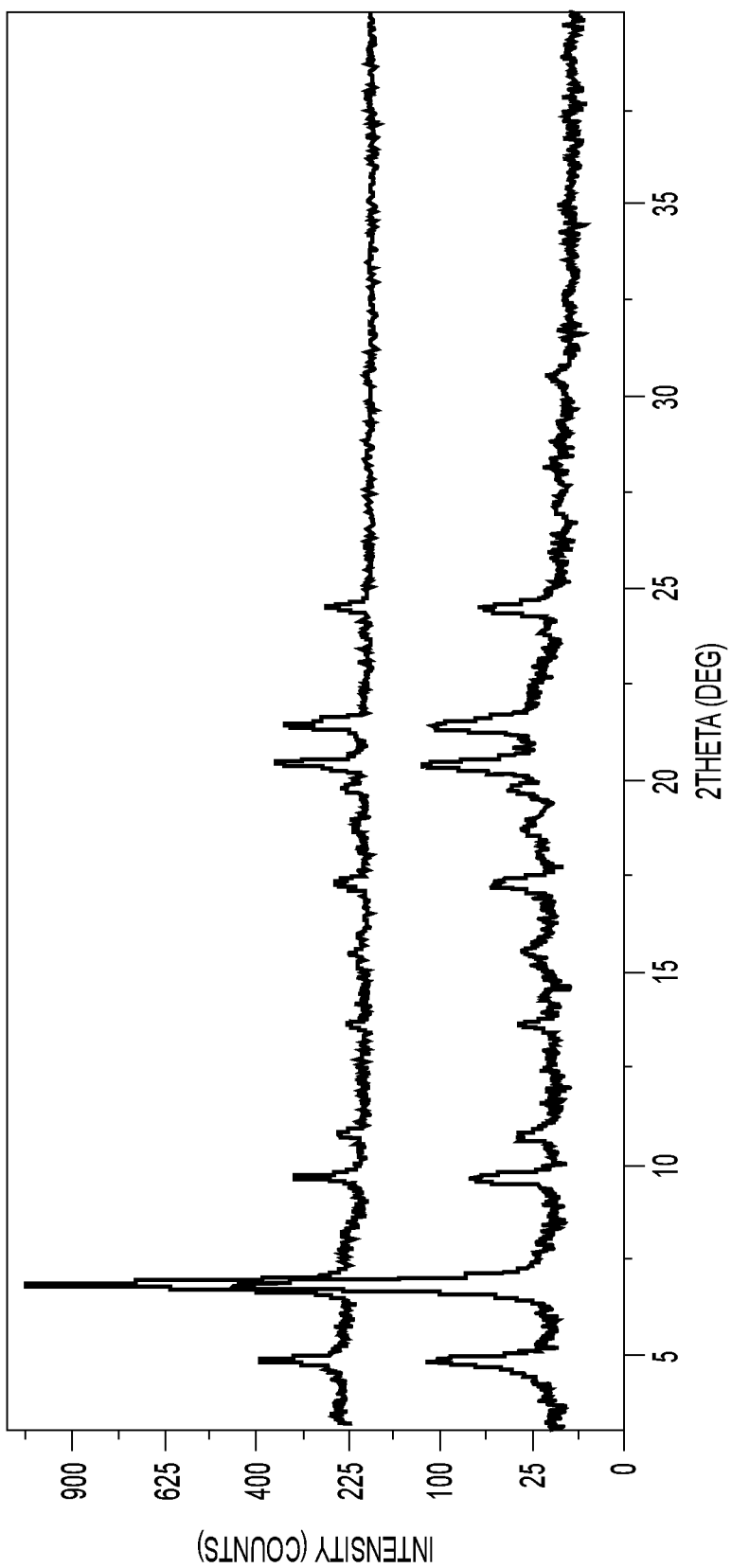
FIG. 17 shows an XRPD pattern overlay of Form CS9 of the present disclosure before and after being stored under 40° C./75% RH for 3 months (from top to bottom: XRPD pattern before storage, XRPD pattern after storage).
Figure 18:
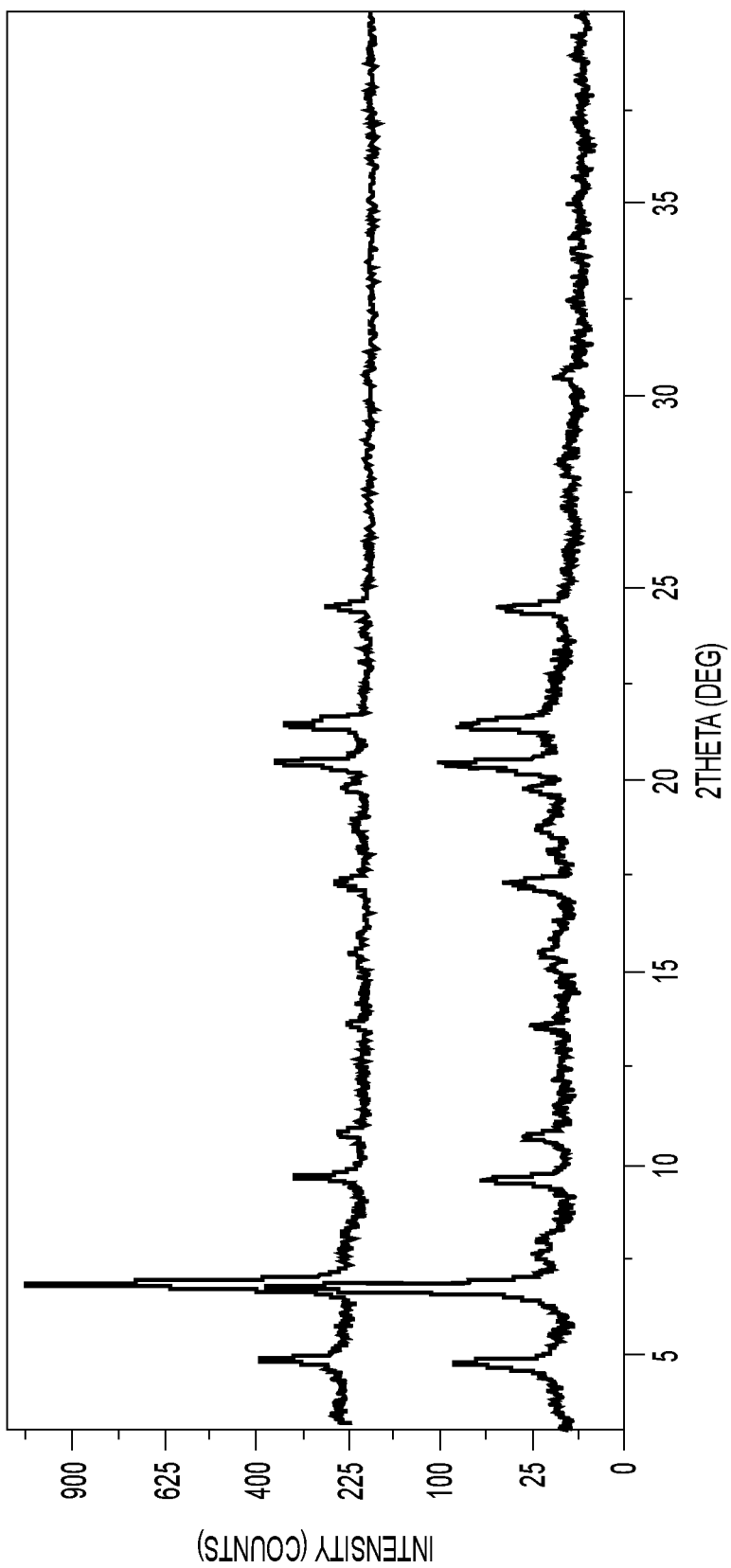
FIG. 18 shows an XRPD pattern overlay of Form CS9 of the present disclosure before and after being stored under 60° C./75% RH for 3 months (from top to bottom: XRPD pattern before storage, XRPD pattern after storage).

Form CS9 was stored under different conditions of 25° C./60% RH, 40° C./75% RH and 60° C./75% RH. The XRPD pattern overlay before and after being stored is substantially as depicted in FIG. 16, FIG. 17 and FIG. 18. The results are shown in Table 9.

TABLE 9

| Initial solid form | Condition | Time | Solid form after storage |
|---|---|---|---|
| Form CS9 (Top of FIG. 16) | 25° C./60% RH | 3 months | Form CS9 (Bottom of FIG. 16) |
| Form CS9 (Top of FIG. 17) | 40° C./75% RH | 3 months | Form CS9 (Bottom of FIG. 17) |
| Form CS9 (Top of FIG. 18) | 60° C./75% RH | 3 months | Form CS9 (Bottom of FIG. 18) |

Furthermore, the inventors also studied the purity change of Form CS9 before and after being stored under the conditions of 25° C./60% RH, 40° C./75% RH and 60° C./75% RH for 1 month, and the results are shown in Table 10.

TABLE 10

| Condition | Initial purity | Purity after 3 months | Purity change |
|---|---|---|---|
| 25° C./60% RH | 99.88% | 99.72% | 0.16% |
| 40° C./75% RH |  | 99.78% | 0.10% |
| 60° C./75% RH |  | 99.76% | 0.12% |

The crystalline form of Form CS9 of the present disclosure doesn't change for at least 3 months and the chemical purity remains for at least 1 month when stored under the condition of 25° C./60% RH, 40° C./75% RH and 60° C./75% RH, indicating that Form CS9 has good physical stability. The crystalline of Form CS9 remains substantially unchanged during storage, which indicates that Form CS9 does not degrade easily, providing a guarantee for the preparation of stable drug products.

Example 11: Kinetic Solubility of Form CS1 and Form CS9

Solubility test method according to the Chinese Pharmacopoeia was used and different pHs of different organs in human body were considered. According to the above two references, a solvent media set with four pH values range from 1.2 to 7.5 were designed in the present disclosure. Specifically: SGF (Simulated gastric fluids, pH=1.8), FeSSIF (Fed state simulated intestinal fluids, pH=5.0), FaSSIF (Fasted state simulated intestinal fluids, pH=6.5), and pure water were used.

Form CS1 and Form CS9 of the present disclosure were suspended into SGF, FeSSIF, FaSSIF and $H_2O$ to obtain saturated solutions. The solutions were sampled at fixed time points. Concentrations of the saturated solutions were measured by HPLC to measure the kinetic solubility of Form CS1 and Form CS9. The results are listed in Table 11 and 12.

TABLE 11

| Kinetic solubility of Form CS1 | | | |
|---|---|---|---|
| Solvent media | Solubility (mg/mL) | | |
|  | 1 h | 4 h | 24 h |
| SGF | 0.0031 | 0.0031 | 0.0030 |
| FeSSIF | 0.19 | 0.19 | 0.16 |
| FaSSIF | 0.063 | 0.050 | 0.027 |
| $H_2O$ | 0.014 | 0.026 | 0.016 |

TABLE 12

Kinetic solubility of Form CS9

| Solvent | Solubility (mg/mL) | | |
|---|---|---|---|
| media | 1 h | 4 h | 24 h |
| SGF | 0.0039 | 0.0042 | 0.0093 |
| FeSSIF | 0.15 | 0.17 | 0.14 |
| FaSSIF | 0.058 | 0.081 | 0.081 |
| H$_2$O | 0.020 | 0.038 | 0.060 |

Solubility is one of the key properties of drug substance, which directly affects the absorption of drugs in human body. The solubility of different crystalline forms may be remarkably different, and the in vivo absorption dynamics may also change, which results in different bioavailability and ultimately affects the clinical safety and efficacy of drugs.

Compound (I) is a poorly water-soluble drug. For poorly water-soluble drug, increasing solubility is even more important. Increase in solubility is conducive to increasing the bioavailability of drugs, thereby increasing the possibility of a successful drug products. In addition, the drug dose reduction without affecting efficacy is possible due to higher solubility, thereby reducing the side effects and improving the safety of drugs.

Form CS1 and Form CS9 of the present disclosure have good solubility in SGF, FeSSIF, FaSSIF and pure water, providing guarantee for the good dissolution of the crystalline drug substance in the drug products, which is beneficial to the in vivo absorption of active ingredients in drugs, achieving ideal bioavailability and efficacy.

Example 12: Flowability of Form CS1 and Form CS9

According to the United States Pharmacopeia (USP) 1174, flowability of Form CS1 and Form CS9 of the present disclosure were evaluated by the compressibility index. The bulk density, tapped density of Form CS1 and Form CS9 were tested, and compressibility index was calculated. The results are listed in Table 13.

1. Test method:
Samples: Form CS1 and Form CS9
Instrument: Tap density tester
Utensil: 5 mL measuring cylinder
Number of tapping: 500 times Bulk density=$m/v_0$(Mass/volume before tapping)

Tapped density=$m/v_t$(Mass/volume after tapping)

2. Calculation formula: compressibility index (%)= (tapped density−bulk density)/tapped density×100%
3. Test results:

TABLE 13

| Form | Bulk density (g/mL) | Tapped density (g/mL) | Compressibility index (%) | Flowability |
|---|---|---|---|---|
| CS1 | 0.15 | 0.19 | 21 | Passable |
| CS9 | 0.11 | 0.14 | 21 | Passable |

* Scale of flowability (according to US Pharmacopoeia 1174); compressibility index ≤10%, excellent flowability; 11%~15%, good flowability; 16%-20%, fair flowability; 21%-25%, passable flowability; 26%~31%, poor flowability; 32%~37%, very poor flowability; >38%, extremely poor flowability.

The results show that the flowability of Form CS1 and Form CS9 of the present disclosure meets the requirements for formulation development, ensures the blend uniformity and content uniformity of the drug products, reduces the weight variation of the drug products and improves product quality, which is suitable for medicinal use.

Example 13: Study of Form CS1 and Form CS9 in Drug Products

1. Preparation of GSK1278863 Tablets:

Form CS1 or Form CS9 of GSK1278863, microcrystalline cellulose, croscarmellose sodium and magnesium stearate were weighed according to formulation in Table 14 and blended for 2 minutes. The tablets were prepared using a manual tablet press at 5KN±1 KN pressure with a φ7 mm round tooling. The tablets tablet weight is 100 mg±1 mg. The obtained tablets were packed in 35 cc HDPE bottles (one tablet per bottle) with 1 g desiccant. The bottles were sealed with a sealer. The crystalline form of Form CS1 and Form CS9 drug substance doesn't change before and after formulation process.

TABLE 14

| Component | Quantity (mg/unit) | Mass ratio (%) |
|---|---|---|
| Form CS1 or Form CS9 | 12.50 | 12.50 |
| Microcrystalline Cellulose | 81.50 | 81.50 |
| Croscarmellose Sodium | 5.00 | 5.00 |
| Magnesium Stearate | 1.00 | 1.00 |
| Total | 100 | 100 |

2. In Vitro Dissolution Profile:

In vitro dissolution test was performed on obtained tablets and dissolution method according to Chinese Pharmacopoeia 2015<0931> was used. The conditions are as follows:

Medium: pH=6.8 phosphate buffer solution+1% sodium dodecyl sulfate aqueous solution
Method: Paddle
Volume: 900 mL
Speed: 75 rpm
Temperature: 37° C.

Figure 19:
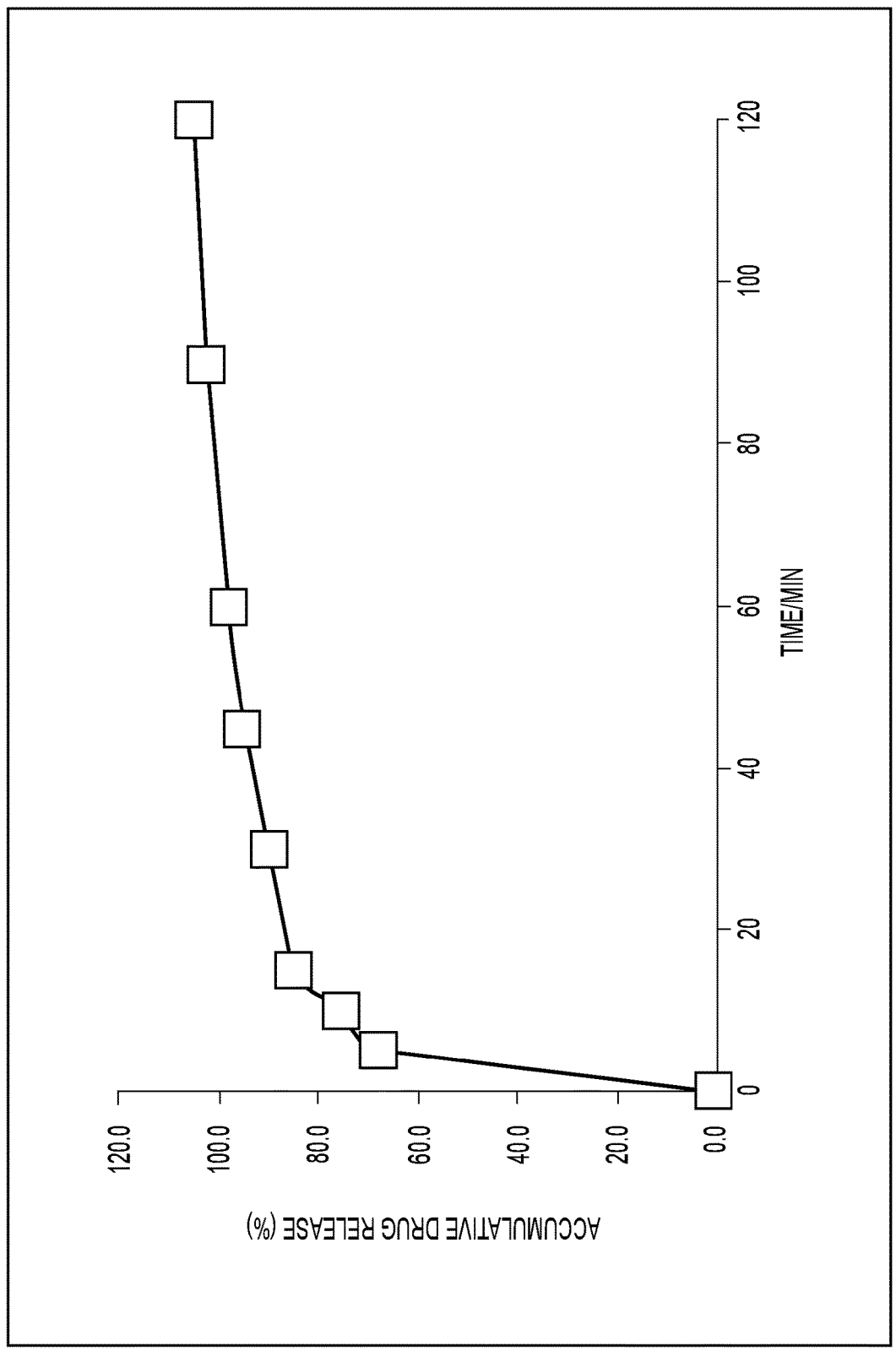
FIG. 19 shows a dissolution profile of a tablet formulation containing Form CS1 of the present disclosure in pH=6.8 phosphate buffer solution.

Dissolution results of Form CS1 are presented in Table 15 and FIG. 19. The results show that the average dissolution of Form CS1 drug products reaches 67.7% at 10 minutes, and the average dissolution reaches 95.2% at 60 minutes, which indicate that Form CS1 drug products possesses favorable dissolution, and fast dissolution rate.

Dissolution is a prerequisite for absorption. Good in vitro dissolution allows drugs to have a higher area under the curve (AUC) in the body, that is, higher in vivo absorption and better in vivo exposure, thereby improving drug's bioavailability and efficacy. High dissolution rate makes the drug have a shorter peak time ($T_{max}$) and a higher peak concentration ($C_{max}$) in the body, which is beneficial for the drug to achieve peak plasma concentration quickly after administration, thus ensuring rapid drug action.

TABLE 15

| Time (min) | Cumulative drug release (%) Form CS1 |
|---|---|
| 5 | 0.0 |
| 10 | 67.7 |
| 20 | 75.8 |
| 30 | 84.8 |
| 45 | 90.1 |

TABLE 15-continued

| Time (min) | Cumulative drug release (%) Form CS1 |
|---|---|
| 60 | 95.2 |
| 90 | 98.3 |
| 120 | 102.5 |

3. Stability of Form CS1 and Form CS9 in Drug Products:

The above obtained tablets were stored under 40° C./675% RH condition for 1 month. After testing, the crystalline form of Form CS1 and Form CS9 drug substance in the drug products does not change. The results are shown in Table 16, which indicate that Form CS1 and Form CS9 have good stability in the drug products.

TABLE 16

Stability of Form CS1 and Form CS9 in drug products

| Sample | Condition | Time | Crystalline forms of API after storage |
|---|---|---|---|
| Tablets with Form CS1 | 40 °C./75% RH | 1 month | Form CS1 |
| Tablets with Form CS9 | 40 °C./75% RH | 1 month | Form CS9 |

Form CS1 and Form CS9 of the present disclosure have good stability in the drug products. Form CS1 and Form CS9 don't readily convert to other crystal forms during the formulation and storage process, ensuring the consistent and controllable quality of drug products.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A composition of crystalline Form CS1 of N-[(1,3-dicyclohexylhexahydro-2,4,6-trioxo-5-pyrimidinyl)carbonyl]-glycine, wherein the X-ray powder diffraction pattern of Form CS1 shows characteristic peaks at 2theta values of 6.4°±0.2°, 7.5°±0.2°, and 7.9°±0.2° using CuKα radiation, and wherein the content of other crystalline forms is less than 10% (w/w).

2. The composition according to claim 1, wherein the X-ray powder diffraction pattern of Form CS1 shows one or more characteristic peaks at 2theta values of 17.2°±0.2°, 21.0°±0.2°, 24.0°±0.2°, and 19.3°±0.2° using CuKα radiation.

3. The composition according to claim 1, wherein the X-ray powder diffraction pattern of Form CS1 is substantially as depicted in FIG. 1.

4. The composition according to claim 1, wherein the Form CS1 has an endothermic peak at around 242° C. as measured by differential scanning calorimetry using a heating rate of 10° C./min and a purge gas of nitrogen.

5. The composition according to claim 1, wherein the chemical purity of Form CS1 is higher than 99%.

6. The composition according to claim 5, wherein the chemical purity remains substantially unchanged when the composition is stored under conditions of 60° C. 75% RH for 3 months.

7. A composition of crystalline Form CS9 of N-[(1,3-dicyclohexylhexahydro-2,4,6-trioxo-5-pyrimidinyl)carbonyl]-glycine, wherein the X-ray powder diffraction pattern of Form CS9 shows characteristic peaks at 2theta values of 4.6°±0.2°, 6.6°±0.2°, and 21.1°±0.2° using CuKα radiation, and wherein the content of other crystalline forms is less than 10% (w/w).

8. The composition according to claim 7, wherein the X-ray powder diffraction pattern of Form CS9 shows one or more characteristic peaks at 2theta values of 9.4°±0.2°, 20.2°±0.2°, and 24.2°±0.2° using CuKα radiation.

9. The composition according to claim 7, wherein the X-ray powder diffraction pattern of Form CS9 is substantially as depicted in FIG. 6.

10. The composition according to claim 7, wherein Form CS9 has a first endothermic peak at around 145° C. and a second endothermic peak at around 237° C. as measured by differential scanning calorimetry using a heating rate of 10° C./min and a purge gas of nitrogen.

11. The composition according to claim 7, wherein the chemical purity of Form CS9 is higher than 99%.

12. The composition according to claim 11, wherein the chemical purity remains substantially unchanged when the composition is stored under conditions of 60° C./75% RH for 1 month.

13. A pharmaceutical composition, wherein said pharmaceutical composition comprises a therapeutically effective amount of the composition of crystalline Form CS1 according to claim 1, and pharmaceutically acceptable carriers, diluents or excipients.

14. A pharmaceutical composition according to claim 13, wherein the crystalline form does not change following one-month storage at 40° C./75% RH.

15. A method of treating anemia, comprising administering to a subject in need thereof a therapeutically effective amount of the composition of crystalline Form CS1 according to claim 1.

16. A pharmaceutical composition, wherein said pharmaceutical composition comprises a therapeutically effective amount of the composition of crystalline Form CS9 according to claim 7, and pharmaceutically acceptable carriers, diluents or excipients.

17. A pharmaceutical composition according to claim 16, wherein the crystalline form does not change following one-month storage at 40° C./75% RH.

18. A method of treating anemia, comprising administering to a subject in need thereof a therapeutically effective amount of the composition of crystalline Form CS9 according to claim 7.

* * * * *